United States Patent
Urch et al.

(10) Patent No.: US 11,019,816 B2
(45) Date of Patent: Jun. 1, 2021

(54) COMPOSITION COMPRISING CINMETHYLIN-CONTAINING MICROPARTICLES AND A FURTHER HERBICIDE

(71) Applicant: BASF Agro B.V., Arnhem (NL)

(72) Inventors: Henning Urch, Limburgerhof (DE); Martina Schmitt, Limburgerhof (DE); Klaus Kolb, Limburgerhof (DE); Diana Franz, Limburgerhof (DE); Evgueni Klimov, Limburgerhof (DE); Helmut Kraus, Research Triangle Park, NC (US)

(73) Assignee: BASF AGRO B.V., Arnhem (NL)

( * ) Notice: Subject to any disclaimer, the term of this patent is extended or adjusted under 35 U.S.C. 154(b) by 0 days.

(21) Appl. No.: 16/476,644

(22) PCT Filed: Jan. 10, 2018

(86) PCT No.: PCT/EP2018/050589
§ 371 (c)(1),
(2) Date: Jul. 9, 2019

(87) PCT Pub. No.: WO2018/130588
PCT Pub. Date: Jul. 19, 2018

(65) Prior Publication Data
US 2019/0373894 A1 Dec. 12, 2019

Related U.S. Application Data
(60) Provisional application No. 62/444,518, filed on Jan. 10, 2017.

(30) Foreign Application Priority Data
Jan. 27, 2017 (EP) .................................. 17153595

(51) Int. Cl.
| | |
|---|---|
| A01N 25/28 | (2006.01) |
| A01N 25/10 | (2006.01) |
| A01N 43/90 | (2006.01) |
| A01N 43/80 | (2006.01) |
| A01N 43/82 | (2006.01) |
| C07D 493/04 | (2006.01) |
| C08G 61/10 | (2006.01) |
| C08L 33/10 | (2006.01) |
| C08L 75/02 | (2006.01) |

(52) U.S. Cl.
CPC ............. *A01N 25/28* (2013.01); *A01N 25/10* (2013.01); *A01N 43/90* (2013.01); *C07D 493/04* (2013.01); *A01N 43/80* (2013.01); *A01N 43/82* (2013.01); *C08G 61/10* (2013.01); *C08L 33/10* (2013.01); *C08L 75/02* (2013.01)

(58) Field of Classification Search
None
See application file for complete search history.

(56) References Cited

U.S. PATENT DOCUMENTS

| | | |
|---|---|---|
| 2008/0234131 A1 | 9/2008 | Gewehr et al. |
| 2014/0221206 A1 | 8/2014 | Formstone et al. |
| 2016/0192645 A1 | 7/2016 | Zhang et al. |
| 2018/0242575 A1* | 8/2018 | Burakowska-Meise ..................... A01N 33/18 |

FOREIGN PATENT DOCUMENTS

| | | | |
|---|---|---|---|
| EP | 3112016 A1 | 1/2017 | |
| WO | 94013139 A1 | 6/1994 | |
| WO | 15165834 A1 | 11/2015 | |
| WO | WO-2015165834 A1 * | 11/2015 | .............. B01J 13/14 |
| WO | 16169795 A1 | 10/2016 | |
| WO | 16202500 A1 | 12/2016 | |
| WO | 16202659 A1 | 12/2016 | |
| WO | 17009054 A1 | 1/2017 | |
| WO | 17009056 A1 | 1/2017 | |
| WO | 17009060 A1 | 1/2017 | |
| WO | 17009061 A1 | 1/2017 | |
| WO | 17009088 A1 | 1/2017 | |
| WO | 17009089 A1 | 1/2017 | |
| WO | 17009090 A1 | 1/2017 | |
| WO | 17009092 A1 | 1/2017 | |
| WO | 17009095 A1 | 1/2017 | |
| WO | 17009124 A1 | 1/2017 | |
| WO | 17009134 A1 | 1/2017 | |
| WO | 17009137 A1 | 1/2017 | |
| WO | 17009138 A1 | 1/2017 | |
| WO | 17009139 A1 | 1/2017 | |
| WO | 17009140 A1 | 1/2017 | |
| WO | 17009142 A1 | 1/2017 | |
| WO | 17009143 A1 | 1/2017 | |
| WO | 17009144 A1 | 1/2017 | |
| WO | 17009145 A1 | 1/2017 | |
| WO | 17009146 A1 | 1/2017 | |
| WO | 17009147 A1 | 1/2017 | |
| WO | 17009148 A1 | 1/2017 | |
| WO | 18104117 A1 | 6/2018 | |
| WO | 18104118 A1 | 6/2018 | |
| WO | 18130589 A1 | 7/2018 | |

OTHER PUBLICATIONS

International Search Report, issued in PCT/EP2018/050589, dated Mar. 2, 2018.

* cited by examiner

*Primary Examiner* — Alton N Pryor
(74) *Attorney, Agent, or Firm* — Marshall, Gerstein & Borun LLP

(57) ABSTRACT

The present invention relates to a composition containing microparticles which comprise cinmethylin and a polymeric material which surrounds or embeds cinmethylin, and at least one herbicide different from cinmethylin. The invention further relates to a method for preparing such compositions and the use of such compositions for controlling undesired vegetation.

14 Claims, No Drawings

COMPOSITION COMPRISING CINMETHYLIN-CONTAINING MICROPARTICLES AND A FURTHER HERBICIDE

This application is a National Stage application of International Application No. PCT/EP2018/050589, filed Jan. 10, 2018, which claims the benefit of U.S. Provisional Application No. 62/444,518, filed Jan. 10, 2017. This application also claims priority under 35 U.S.C. § 119 to European Patent Application No. 17153595.8, filed Jan. 27, 2017.

The present invention relates to a composition containing microparticles which comprise cinmethylin and a polymeric material which surrounds or embeds cinmethylin, and at least one herbicide different from cinmethylin. The invention further relates to a method for preparing such compositions and the use of such compositions for controlling undesired vegetation.

BACKGROUND OF THE INVENTION

In crop protection, it is desirable to increase the specific activity of an active compound and the reliability of the effect. In the control of undesired vegetation, it is particularly desirable for the crop protection product to control the harmful plants effectively, but at the same time to be compatible with the useful plants in question. Also desirable is a broad spectrum of activity allowing the simultaneous control of various harmful plants. Frequently, this cannot be achieved using a single herbicidally active compound. Further, cases of herbicide-resistant weeds are becoming increasingly common. These biotypes survive herbicide application at doses that usually give effective control of the species. Herbicide resistance is often avoided by combining different herbicidally active agents.

In practice, combining different herbicidally active compounds may however represent a major challenge, as many active compounds are not compatible with each other, especially in liquid product formulations, such as solutions, suspensions or emulsions. Liquid formulations are however a desirable product form, as they have a number of advantages in comparison with solid forms such as powders, dusts or granules, for example no dust development, improved wetting properties and, generally, a better ability to be measured into exact doses. Moreover, active compounds which are not solid cannot easily be incorporated into solid formulations.

If active compounds are not compatible with each other in liquid formulations, this may become manifest, for example, in sediment formation, agglomeration, crystallization and/or syneresis (deposition of liquid formulation constituents). In other cases, the phytotoxicity on cultivated plants may be enhanced by the combination of two or more active compounds in a liquid formulation.

One may try to solve this problem by the separate formulation of different active substances, but this is firstly disadvantageous for commercialization reasons and secondly might just shift the incompatibility problem to the tank mix. A sediment formation etc. in the tank might be even more problematic than in the commercial formulation. Moreover, certain incompatibility problems, such as enhanced phytotoxicity caused by the combination of two or more active compounds, especially if one active compound can dissolve the other active compound and increase its potency, are generally not solved by a separate formulation.

Cinmethylin is a selective, pre-emergence, systemic herbicide useful for the control of annual grass weeds, for example in rice. It is desirable to combine this herbicide with various other herbicides, for example in order to increase its activity spectrum and/or avoid resistance formation.

As the present inventors however found, the combination of cinmethylin with various other herbicides may have major drawbacks. For instance, combining cinmethylin with quinmerac in a suspoemulsion (cinmethylin is an oily liquid and thus generally provided as an emulsion concentrate (EC), while quinmerac is a water-insoluble solid and thus typically formulated as a suspension concentrate (SC), a natural combination of the two formulations thus being a suspoemulsion) leads to strong crystal growth of the quinmerac particles and Ostwald ripening after storage. The problem with Ostwald ripening also occurs when cinmethylin is combined with flufenacet or diflufenican in a suspoemulsion or in an emulsion concentrate. Combining cinmethylin with picolinafen in an emulsion concentrate (both active compounds are typically formulated as EC) leads to a severe increase of the phytotoxicity on cultivated plants.

WO 94/13139 describes microcapsules containing a pesticide core and a shell of polyurea, polyamide, polysulfonamide, polyester, polycarbonate or polyurethane. Inter alia, microcapsules comprising cinmethylin and a shell made of polyureas obtained by the reaction of hexamethylenediamine and PAPI® 2027 (a polymethylene polyphenylisocyanate from Dow Chemical) are described. The combination with other herbicides is not described. The aqueous phase used in the capsule preparation method of this reference contains a specific emulsifier which is a water-soluble random co- or terpolymer of vinylpyrrolidone. Such vinylpyrrolidone co-/terpolymers are rather expensive, which is of course economically disadvantageous for mass products such as pesticide formulations, and their ecologically compatibility is rather low. The preferably used quaternary copolymers are even classified as aquatoxic.

WO 2015/165834 relates to a process for producing microcapsules with a core of a water-insoluble material comprising a pesticide. Inter alia, the preparation of microcapsules comprising cinmethylin is described, the shell of which is made of polyureas obtained by the reaction of Bayhydur® XP 2547 (an anionic water-dispersible polyisocyanate based on hexamethylene diisocyanate), dicyclohexylmethane diisocyanate and a polyethyleneimine.

It was the object of the present invention to provide a composition containing cinmethylin and at least one further herbicide which does not have the above-described drawbacks. At the same time, the release profile should still allow a good initial biological activity of the composition, i.e. the composition should release the active compounds at a sufficiently high rate.

It was also desirable to provide a composition which could dispense with the use/presence of the vinylpyrrolidone co- or terpolymer emulsifiers as used in WO 94/13139, but still contains cinmethylin in high concentrations.

It was surprisingly found that a composition containing microparticles which comprise cinmethylin and a polymeric material which surrounds or embeds cinmethylin, and further contains at least one further herbicide (the further herbicide being of course not in the microparticles) solve the above problems.

SUMMARY OF THE INVENTION

In a first aspect, the invention thus relates to a composition comprising (a) microparticles which comprise cinmethylin and a polymeric material which surrounds or embeds cinmethylin; and
(b) at least one herbicide different from cinmethylin.

As said, the at least one herbicide different from cinmethylin is of course not present in the microparticles.

In another aspect, the invention relates to a method for preparing the composition of the invention, comprising providing microparticles which comprise cinmethylin and a polymeric material which surrounds or embeds cinmethylin, and mixing the latter with the at least one herbicide different from cinmethylin. In particular, the method comprises polymerizing one or more monomers or curing a prepolymer or pre-condensate in the presence of cinmethylin, and mixing with the at least one herbicide different from cinmethylin.

In yet another aspect, the invention relates to the use of the composition of the invention for controlling undesired vegetation, and to a method for controlling undesired vegetation comprising treating the soil in which undesired vegetation is growing and/or undesired vegetation and/or cultivated plants to be protected from undesired vegetation and/or on their environment with the composition of the invention.

DETAILED DESCRIPTION OF THE INVENTION

The organic moieties mentioned in the following are collective terms for individual listings of the individual group members. The prefix $C_n$-$C_m$ indicates in each case the possible number of carbon atoms in the group.

The term "$C_1$-$C_{10}$-alkyl" refers to saturated straight-chain or branched aliphatic radicals having 1 to 10 carbon atoms. Examples are methyl, ethyl, n-propyl, isopropyl, n-butyl, 1-methylpropyl (sec-butyl), 2-methylpropyl (isobutyl), 1,1-dimethylethyl (tert-butyl), n-pentyl, 1-methylbutyl, 2-methylbutyl, 3-methylbutyl, 2,2-dimethylpropyl, 1-ethylpropyl, 1,1-dimethylpropyl, 1,2-dimethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl, decyl, 2-propylheptyl and structural isomers thereof.

The term "$C_1$-$C_{24}$-alkyl" refers to saturated straight-chain or branched aliphatic radicals having 1 to 24 carbon atoms. Examples are methyl, ethyl, n-propyl, isopropyl, n-butyl, 1-methylpropyl (sec-butyl), 2-methylpropyl (isobutyl), 1,1-dimethylethyl (tert-butyl), n-pentyl, 1-methylbutyl, 2-methylbutyl, 3-methylbutyl, 2,2-dimethylpropyl, 1-ethylpropyl, 1,1-dimethylpropyl, 1,2-dimethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl, decyl, 2-propylheptyl, undecyl, dodecyl, tridecyl, tetradecyl, pentadecyl, hexadecyl, heptadecyl, octadecyl, nonadecyl, eicosyl, henicosyl, docosyl, tricosyl, tetracosyl and structural isomers thereof.

$C_1$-$C_4$-Alkanols are methanol, ethanol, n-propanol, isopropanol, n-butanol, sec-butanol, isobutanol and tert-butanol.

$C_2$-$C_4$-Alkanediols are alkanes having 2 to 4 carbon atoms and carrying two OH groups which are not bound to the same carbon atom. Examples are ethyleneglycol (ethane-1,2-diol), propyleneglycol (propane-1,2-diol), propane-1,3-diol, butane-1,2-diol, butane-1,3-diol, butane-1,4-diol and butane-2,3-diol. $C_2$-$C_5$-Alkanediols are alkanes having 2 to 5 carbon atoms and carrying two OH groups which are not bound to the same carbon atom. Examples are those mentioned for $C_2$-$C_4$-alkanediols, and additionally pentane 1,5-diol.

$C_3$-$C_8$-Alkanetriols are alkanes having 3 to 8 carbon atoms and carrying three OH groups which are all bound to different carbon atoms. Examples are glycerol (1,2,3-propanetriol), 1,2,4-butanetriol, 1,2,3- or 1,2,6-hexanetriol, 1,2,3-heptanetriol and 1,2,3-octanetriol.

$C_{10}$-$C_{22}$ Fatty acids are aliphatic, saturated or unsaturated monocarboxylic acids with 10 to 22 carbon atoms (the carboxylic group is included in this count, where the carbon chain is mostly linear. Examples for saturated $C_{10}$-$C_{22}$ fatty acids are decanoic acid (capric acid), undecanoic acid, lauric acid, tridecanoic acid, myristic acid, pentadecanoic acid, palmitic acid, heptadecanoic acid, stearic acid, nonadecanoic acid, arachidic acid, heneicosanoic acid and behenic acid. Examples for unsaturated $C_{10}$-$C_{22}$ fatty acids are myristoleic acid, palmitoleic acid, oleic acid, elaidic acid, erucic acid, linoleic acid, α- and γ-linolenic acid, and arachidonic acid.

Microparticles are particles with a particle size below 1 mm.

Preferably, the average particle size $d_{50}$ of the microparticles is from 0.05 to 100 µm, more preferably from 0.05 to 20 µm, in particular from 0.05 to 12 µm, and specifically from 0.05 to 10 µm.

In the microparticles cinmethylin is surrounded by or embedded in a polymeric material. The polymeric material may form a regular or irregular shell which surrounds cinmethylin or may form a polymer matrix in which cinmethylin is embedded. Cinmethylin may be completely or only partly be surrounded by or embedded in the polymeric material. In particular, the polymeric material will completely surround cinmethylin, thereby forming a barrier between this substance and the surrounding medium, thus separating cinmethylin from the other at least one herbicide either in the composition of the invention, if this is a physical mixture of the microparticles and the at least one herbicide different from cinmethylin, or in the tankmix, if the composition of the invention is not a physical mixture of the microparticles and the at least one herbicide different from cinmethylin and these are to be mixed shortly before application, or on the locus of application, if the microparticles and the at least one herbicide different from cinmethylin are applied separately (but of course time- and locus-related).

In a particular embodiment, the microparticles are microcapsules. Microcapsules are spherical objects which consist of a core and shell, i.e. a wall material surrounding the core. In the microcapsules of the invention, the core contains cinmethylin. The shell comprises a polymeric material. The microcapsules usually have a particle size in the range from 0.1 to 1000 µm, preferably from 0.5 to 100 µm, more preferably from 1 to 20 µm, in particular from 2 to 12 µm, and specifically from 5 to 10 µm.

In another particular embodiment, the microparticles are matrix particles, i.e. amorphous particles which contain cinmethylin embedded in a polymer matrix. Such matrix particles have often very small particles sizes, e.g. from 50 nm to 1 µm, preferably from 50 to 500 nm, in particular from 50 to 300 nm and specifically from 100 to 200 nm. Although often in the nanometer scale, they are herein nevertheless termed "microparticles".

The microparticles can also take a mixed form thereof, i.e. can be a mixture of microcapsules and matrix particles.

Unless specified otherwise, the particle sizes given above and below are the average particle diameters or average particle sizes, herein also termed $d_{50}$ value. The $d_{50}$ value is defined as the value that is above the diameters of 50% by weight of the particles and below the diameters of 50% by weight of the particles. The $d_{50}$ value can be calculated from the particle size distribution of the microparticles. The particle size distribution of the microparticles (i.e. the diameters) can be determined for example by conventional methods such as dynamic or static light-scattering of an aqueous dispersion of the microparticle composition, e.g. at 25° C. and a concentration in the range of 0.1 to 1% by weight. Herein, the $d_{50}$ value is determined according to ISO 13320, Particle Size Analysis—Laser Diffraction Methods, Dec. 1, 2009.

In some instances below, the $d_{90}$ value or the $d_{10}$ value is given. The $d_{90}$ value has to be understood as the value that is not exceeded by the diameters of at least 90% by weight of the microparticles, and the $d_{10}$ value as the value of diameters which at least 10% by weight of the microparticles exceed. The $d_{90}$ and $d_{10}$ values, like the $d_{50}$ value, can be calculated from the particle size distribution of the microparticles. Further details are given above.

Preferably, the microparticles are microcapsules.

In the terms of the present invention "composition" is not restricted to a physical mixture (co-formulation) containing the microparticles and the at least one herbicide different from cinmethylin, but refers to any preparation form of the microparticles and the at least one herbicide different from cinmethylin, the use of which is time- and locus-related. In one embodiment of the invention "composition" refers to a physical mixture of the microparticles and the at least one herbicide different from cinmethylin. In another embodiment of the invention, "composition" refers to the microparticles and the at least one herbicide different from cinmethylin being formulated separately, but in such a form that they can be applied to the soil in which undesired vegetation is growing and/or undesired vegetation and/or cultivated plants to be protected from undesired vegetation and/or on their environment in a temporal relationship, i.e. simultaneously or subsequently, the subsequent application having a time interval which allows a combined action of the two components.

One example for a composition wherein the microparticles and the at least one herbicide different from cinmethylin are formulated separately is a combipack. In a combipack, two or more components of the combipack are packaged separately, i.e., not jointly pre-formulated. As such, combipacks include one or more separate containers such as vials, cans, bottles, pouches, bags or canisters, each container containing a separate component for an agrochemical composition. One example is a two-component combipack (two-component-kit). In this case, the advantages of the composition of the invention become manifest in the tankmix, if the microparticles and the at least one herbicide different from cinmethylin are to be mixed shortly before application, or on the locus of application, if they are applied separately (but of course time- and locus-related).

"Time-related" means that the time interval between the separate application of the two or more herbicides (cinmethylin and the at least one other herbicide) is such that the active compound applied first is still present on the locus of application when the second is applied. This time interval is generally from a few seconds to a few days, e.g. from 1 s to 7 days or from 1 s to 24 h or from 1 s to 12 h.

Preferably however, the composition of the invention is a physical mixture (co-formulation) containing both the microparticles and the at least one herbicide different from cinmethylin.

The common name cinmethylin as used herein refers to the racemic mixture (±)-2-exo-(2-methyl benzyloxy)-1-methyl-4-isopropyl-7-oxabicyclo[2.2.1]heptane (also referred to as the "exo-(±)-isomers", CAS RN 87818-31-3)

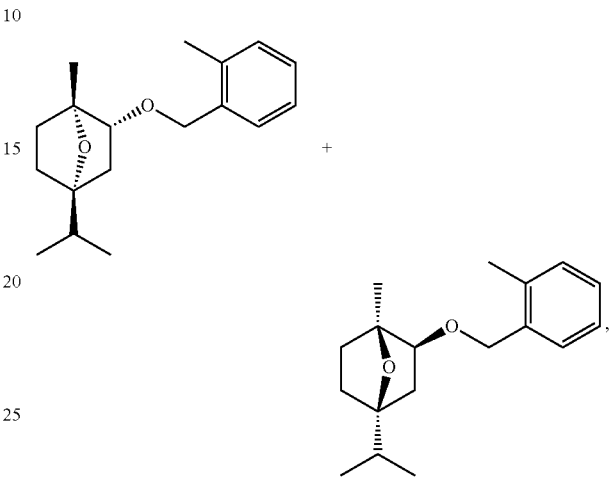

to any of its individual enantiomers or to any non-racemic mixture thereof. The racemic mixture contains equal parts of the two enantiomers (+)-2-exo-(2-methylbenzyloxy)-1-methyl-4-isopropyl-7-oxabicyclo[2.2.1]heptane (also referred to as the "exo-(+)-isomer", CAS RN 87818-61-9) and (−)-2-exo-(2-methylbenzyloxy)-1-methyl-4-isopropyl-7-oxabicyclo[2.2.1]heptane (also referred to as the "exo-(−)-isomer", CAS RN 87819-60-1). The exo-(±)-isomers, the exo-(+)-isomer and the exo-(−)-isomer including their preparation and herbicidal properties are disclosed in EP 0 081 893 A2 (see examples 29, 34, 35 and 62). Further preparation methods of these compounds are described in U.S. Pat. No. 4,487,945 (see embodiments 46 and 48). The racemic mixture (±)-2-exo-(2-methylbenzyloxy)-1-methyl-4-isopropyl-7-oxabicyclo[2.2.1]heptane is also described in The Pesticide Manual, Fourteenth Edition, Editor: C. D. S. Tomlin, British Crop Production Council, 2006, entry 157, pages 195-196 with its IUPAC name (1RS,2SR,4SR)-1,4-epoxy-p-menth-2-yl 2-methylbenzyl ether and its Chemical Abstracts name exo-(±)-1-methyl-4-(1-methylethyl)-2-[(2-methyl phenyl)methoxy]-7-oxabicyclo[2.2.1]heptane. Cinmethylin is a liquid, which is barely soluble in water (0.063 g·L$^{-1}$ at 20° C.), but soluble in organic solvents. It has a boiling point of 312° C. (Pesticide Science, 1987, 21, Nr. 2, 143-153).

The at least one herbicide different from cinmethylin is typically an herbicide which, when formulated together with cinmethylin as such, would lead to a formulation with the above-described disadvantages.

Preferably, the at least one herbicide different from cinmethylin is selected from the group consisting of:
(b1) herbicides from the group of the lipid biosynthesis inhibitors, which are in turn selected from the group consisting of:
ACC-herbicides selected from the group consisting of alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); and
non ACC herbicides selected from the group consisting of benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;
(b2) herbicides from the group of the ALS inhibitors, which are in turn selected from the group consisting of:
sulfonylureas selected from the group consisting of amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron,
imidazolinones selected from the group consisting of imazamethabenz, imazamethabenz-methyl, imazamox, imazapic, imazapyr, imazaquin and imazethapyr,
triazolopyrimidine herbicides and sulfonanilides selected from the group consisting of cloransulam, cloransulam-methyl, diclosulam, flumetsulam, florasulam, metosulam, penoxsulam, pyrimisulfan and pyroxsulam, pyrimidinylbenzoates selected from the group consisting of bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5), and N-(4-bromophenyl)-2-[(4,6-dimethoxy-2-pyrimidinyl)oxy]benzenemethanamine (CAS 420138-01-8), sulfonylaminocarbonyl-triazolinone herbicides selected from the group consisting of flucarbazone, flucarbazone-sodium, propoxycarbazone, propoxycarbazone-sodium, thiencarbazone and thiencarbazone-methyl; and triafamone;
(b3) herbicides from the group of the photosynthesis inhibitors, which are in turn selected from the group consisting of:
amicarbazone,
inhibitors of the photosystem II selected from the group consisting of triazine herbicides, in turn selected from the group consisting of chlorotriazine, triazinones, triazindiones, methylthiotriazines and pyridazinones in turn selected from the group consisting of ametryn, atrazine, chloridazone, cyanazine, desmetryn, dimethametryn, hexazinone, metribuzin, prometon, prometryn, propazine, simazine, simetryn, terbumeton, terbuthylazin, terbutryn and trietazin, aryl urea herbicides selected from the group consisting of chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron,
phenyl carbamates selected from the group consisting of desmedipham, karbutilat, phenmedipham and phenmedipham-ethyl,
nitrile herbicides selected from the group consisting of bromofenoxim, bromoxynil and its salts and esters, and ioxynil and its salts and esters,
uraciles selected from the group consisting of bromacil, lenacil and terbacil, bentazon and bentazon-sodium, pyridate, pyridafol, pentanochlor, propanil and inhibitors of the photosystem I selected from the group consisting of diquat, diquat-dibromide, paraquat, paraquat-dichloride and paraquat-dimetilsulfate;
(b4) herbicides from the group of the protoporphyrinogen-IX oxidase inhibitors, which are in turn selected from the group consisting of:
acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, trifludimoxazin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethyl phenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7), 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0), 1-methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0), methyl (E)-4-[2-chloro-5-[4-chloro-5-(difluoromethoxy)-1H-methyl-pyrazol-3-yl]-4-fluoro-phenoxy]-3-methoxy-but-2-enoate (CAS 948893-00-3), and 3-[7-chloro-5-fluoro-2-(trifluoromethyl)-1H-benzimidazol-4-yl]-1-methyl-6-(trifluoromethyl)-1H-pyrimidine-2,4-dione (CAS 212754-02-4);

(b5) herbicides from the group of the bleacher herbicides, which are in turn selected from the group consisting of:
PDS inhibitors selected from the group consisting of beflubutamid, diflufenican, fluridone, flurochloridone, flurtamone, norflurazon, picolinafen, and 4-(3-trifluoromethylphenoxy)-2-(4-trifluoromethylphenyl)pyrimidine (CAS 180608-33-7),
HPPD inhibitors selected from the group consisting of benzobicyclon, benzofenap, bicyclopyrone, clomazone, fenquinotrione, isoxaflutole, mesotrione, oxotrione (CAS 1486617-21-3), pyrasulfotole, pyrazolynate, pyrazoxyfen, sulcotrione, tefuryltrione, tembotrione, tolpyralate and topramezone;
aclonifen, amitrole flumeturon and 2-chloro-3-methylsulfanyl-N-(1-methyltetrazol-5-yl)-4-(trifluoromethyl)benzamide;

(b6) herbicides from the group of the EPSP synthase inhibitors, which are in turn selected from the group consisting of:
glyphosate, glyphosate-isopropylammonium, glyposate-potassium and glyphosate-trimesium (sulfosate);

(b7) herbicides from the group of the glutamine synthase inhibitors, which are in turn selected from the group consisting of:
bilanaphos (bialaphos), bilanaphos-sodium, glufosinate, glufosinate-P and glufosinate-ammonium;

(b8) the DHP synthase inhibitor herbicide asulam;

(b9) herbicides from the group of the mitosis inhibitors, which are in turn selected from the group consisting of:
compounds of group K1 selected from the group consisting of dinitroanilines in turn selected from the group consisting of benfluralin, butralin, dinitramine, ethalfluralin, fluchloralin, oryzalin, pendimethalin, prodiamine and trifluralin, phosphoramidates selected from the group consisting of amiprophos, amiprophos-methyl, and butamiphos,
benzoic acid herbicides selected from the group consisting of chlorthal and chlorthal-dimethyl,
pyridines selected from the group consisting of dithiopyr and thiazopyr, benzamides selected from the group consisting of propyzamide and tebutam; compounds of group K2 selected from the group consisting of carbetamide, chlorpropham, flamprop, flamprop-isopropyl, flamprop-methyl, flamprop-M-isopropyl, flamprop-M-methyl and propham;

(b10) herbicides from the group of the VLCFA inhibitors, which are in turn selected from the group consisting of:
chloroacetamides selected from the group consisting of acetochlor, alachlor, butachlor, dimethachlor, dimethenamid, dimethenamid-P, metazachlor, metolachlor, metolachlor-S, pethoxamid, pretilachlor, propachlor, propisochlor and thenylchlor,
oxyacetanilides selected from the group consisting of flufenacet and mefenacet, acetanilides selected from the group consisting of diphenamid, naproanilide, napropamide and napropamide-M,
the tetrazolinone herbicide fentrazamide; and
other herbicides selected from the group consisting of anilofos, cafenstrole, fenoxasulfone, ipfencarbazone, piperophos, pyroxasulfone and isoxazoline compounds of the formulae II.1, II.2, II.3, II.4, II.5, II.6, II.7, II.8 and II.9

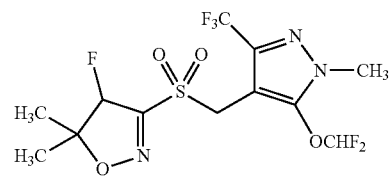

II.1

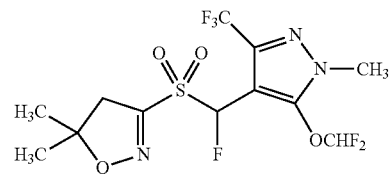

II.2

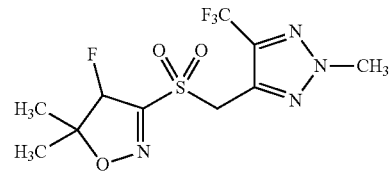

II.3

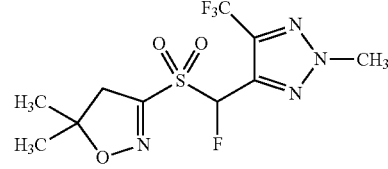

II.4

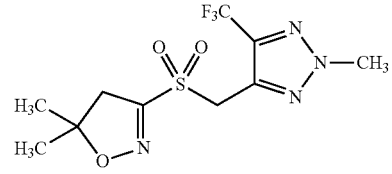

II.5

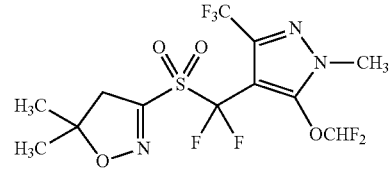

II.6

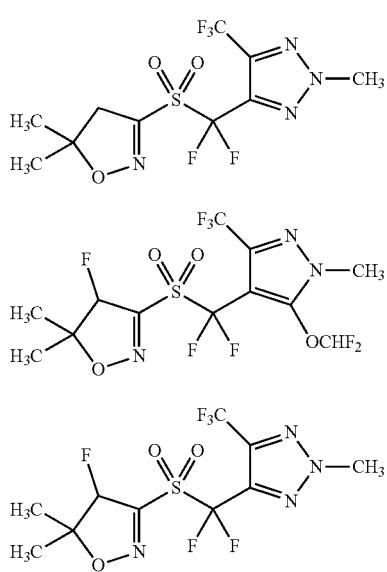

(b11) herbicides from the group of the cellulose biosynthesis inhibitors, which are in turn selected from the group consisting of:
chlorthiamid, dichlobenil, flupoxam, indaziflam, isoxaben, triaziflam and 1-cyclohexyl-5-pentafluorphenyloxy-1⁴-[1,2,4,6]thiatriazin-3-ylamine (CAS 175899-01-1);

(b12) herbicides from the group of the decoupler herbicides, which are in turn selected from the group consisting of:
dinoseb, dinoterb and DNOC and its salts;

(b13) herbicides from the group of the auxinic herbicides, which are in turn selected from the group consisting of:
2,4-D and its salts and esters such as clacyfos, 2,4-DB and its salts and esters, aminocyclopyrachlor and its salts and esters, aminopyralid and its salts such as aminopyralid-dimethylammonium, aminopyralid-tris(2-hydroxypropyl)ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, flopyrauxifen, fluroxypyr, fluroxypyr-butometyl, fluroxypyr-meptyl, halauxifen and its salts and esters (CAS 943832-60-8); MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters, triclopyr and its salts and esters, 4-amino-3-chloro-6-(4-chloro-2-fluoro-3-methoxyphenyl)-5-fluoropyridine-2-carboxylic acid, benzyl 4-amino-3-chloro-6-(4-chloro-2-fluoro-3-methoxyphenyl)-5-fluoropyridine-2-carboxylate (CAS 1390661-72-9) and 4-amino-3-chloro-5-fluoro-6-(7-fluoro-1H-indol-6-yl)picolinic acid;

(b14) herbicides from the group of the auxin transport inhibitors, which are in turn selected from the group consisting of:
diflufenzopyr, diflufenzopyr-sodium, naptalam and naptalam-sodium; and (b15) other herbicides selected from the group consisting of:
bromobutide, chlorflurenol, chlorflurenol-methyl, cumyluron, cyclopyrimorate (CAS 499223-49-3) and its salts and esters, dalapon, dazomet, difenzoquat, difenzoquat-metilsulfate, dimethipin, DSMA, dymron, endothal and its salts, etobenzanid, flurenol, flurenol-butyl, flurprimidol, fosamine, fosamine-ammonium, indanofan, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine and tridiphane.

More preferably, the at least one herbicide different from cinmethylin is selected from the group consisting of quinmerac, picolinafen, dimethenamid, dimethenamid-P, imazamox, diflufenican, flufenacet, pendimethalin, pyroxasulfone, sulfonylureas selected from the group consisting of amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron, and aminopyralid and its salts.

Even more preferably, the at least one herbicide different from cinmethylin is selected from the group consisting of quinmerac, picolinafen, dimethenamid, dimethenamid-P, diflufenican, flufenacet and pendimethalin, and in particular from the group consisting of quinmerac, picolinafen, diflufenican and flufenacet. Specifically, the at least one herbicide different from cinmethylin is selected from the group consisting of quinmerac and picolinafen.

Thus, in a particular embodiment, the composition of the invention comprises microparticles which comprise cinmethylin and a polymeric material which surrounds or embeds cinmethylin; and quinmerac.

In another particular embodiment, the composition of the invention comprises microparticles which comprise cinmethylin and a polymeric material which surrounds or embeds cinmethylin; and picolinafen.

In another particular embodiment, the composition of the invention comprises microparticles which comprise cinmethylin and a polymeric material which surrounds or embeds cinmethylin; and diflufenican.

In another particular embodiment, the composition of the invention comprises microparticles which comprise cinmethylin and a polymeric material which surrounds or embeds cinmethylin; and flufenacet.

In the composition of the invention, cinmethylin and the at least one herbicide different therefrom are present in an overall weight ratio of preferably from 100:1 to 1:100, in particular from 50:1 to 1:50, and specifically from 10:1 to 1:10. "Overall" means that the weight ratio refers to the weight of all herbicides different from cinmethylin, should more than one be used.

As said above, in a preferred embodiment, the microparticles are microcapsules.

The microcapsules comprise a shell and a core, where the core contains cinmethylin. The core may also comprise a solvent. If this is the case, cinmethylin may be present in the core in dissolved form or as an emulsion.

"Solvent" is a liquid substance that dissolves a solute (a chemically different liquid, solid or gas), resulting in a solution. In the present context, the term "solvent" is however not restricted to a compound or medium which dissolves cinmethylin in the proper sense: This compound or medium may be more generally a dispersing medium, and thus the "solution" might be an emulsion or a solution in the proper sense (the latter being a homogeneous mixture composed of two or more substances, where the particles of the solute cannot be seen by naked eye and which does not scatter light).

Any solvent, if present in the core, is preferably selected from water immiscible organic solvents, water, water miscible organic solvents and mixtures thereof.

The solvent, if present, is preferably a water immiscible organic solvent. Water immiscible organic solvents in this context are solvents with a solubility in water at 20° C. of at most 20 g/L, preferably of at most 5 g/L and in particular of at most 0.5 g/L.

Suitable examples for water immiscible organic solvents are
- a hydrocarbon solvent such a an aliphatic, cyclic and aromatic hydrocarbon (e.g. toluene, xylene, paraffin, tetrahydronaphthalene, alkylated naphthalenes or their derivatives, mineral oil fractions of medium to high boiling point (such as kerosene, diesel oil, coal tar oils));
- a vegetable oil such as corn oil, rapeseed oil;
- a fatty acid ester such as $C_1$-$C_{10}$-alkylester of a $C_{10}$-$C_{22}$-fatty acid;
- methyl- or ethyl esters of vegetable oils such as rapeseed oil methyl ester or corn oil methyl ester;
- partly saponified fats or oils; or
- rosins or rosin oils.

Mixtures of aforementioned water immiscible organic solvents are also possible. The water immiscible organic solvent is usually commercially available, such as the hydrocarbons under the tradenames Solvesso® 200, Aromatic® 200, or Caromax® 28. The aromatic hydrocarbons may be used as naphthalene depleted qualities. Preferred water immiscible organic solvents are hydrocarbons, in particular aromatic hydrocarbons.

Frequently, the water immiscible organic solvent, if present, has a boiling point above 100° C., preferably above 150° C., and in particular above 180° C.

If a water immiscible organic solvent is present in the core of the microcapsule, this is preferably comprised in an amount of up to 10% by weight, more preferably up to 5% by weight, and in particular up to 1% by weight, relative to the total weight of the core.

Preferably, the core of the microcapsule comprises less than 1% by weight, preferably less than 0.5% by weight, and in particular less than 0.1% by weight of the water immiscible organic solvent, relative to the total weight of the core.

Specifically, the core of the microcapsule is free of the water immiscible organic solvent.

Additionally or alternatively, the core of the microcapsules may comprise water, water miscible organic solvents or mixtures thereof. Water miscible organic solvents in this context are solvents with a solubility in water at 20° C. of more than 20 g/L. Examples for water miscible organic solvents are $C_1$-$C_3$-alkanols, i.e. methanol, ethanol, propanol or isopropanol, polyols, such as ethylene glycol, diethylene glycol, triethylene glycol or glycerine, cyclic ethers, such as the dioxanes and tetrahydrofuran, acetone, dimethylsulfoxide, amides, such as dimethylformamide and dimethylacetamide, benzoyllactate, lactams, such as N-butylpyrrolidone and N-formylpyrrolidone, N-formylmorpholine and propylenecarbonate.

If water or a water miscible organic solvent is present in the core of the microcapsule, this is preferably comprised in an amount of up to 10% by weight, more preferably up to 5% by weight, and in particular up to 1% by weight, relative to the total weight of the core.

Preferably, the core of the microcapsule comprises less than 1% by weight, preferably less than 0.5% by weight, and in particular less than 0.1% by weight of water and the water miscible organic solvent, relative to the total weight of the core.

Specifically, the core of the microcapsule is free of water and the water miscible organic solvent.

If a mixture of one or more water immiscible organic solvents, water and/or one or more water miscible organic solvents is present in the core of the microcapsule, these are preferably comprised in an overall amount of up to 10% by weight, more preferably up to 5% by weight, and in particular up to 1% by weight, relative to the total weight of the core.

Preferably, the core of the microcapsule comprises less than 1% by weight, preferably less than 0.5% by weight, and in particular less than 0.1% by weight of water immiscible organic solvent, water and water miscible organic solvent, relative to the total weight of the core.

Specifically, the core of the microcapsule is free of water immiscible organic solvents, water and water miscible organic solvents.

The core may optionally contain auxiliaries, such as organic modified polysiloxanes such as Break Thru S 240@; alcohol alkoxylates such as Atplus® 245, Atplus® MBA 1303, Plurafac® LF 300 and Lutensol® ON 30; EO/PO block polymers, Poloxamers, e.g. Pluronic® RPE 2035 and Genapol® B; alcohol ethoxylates such as Lutensol® XP 80; and dioctyl sulfosuccinate sodium such as Leophen® RA. If such auxiliaries are present in the core of the microcapsule, these are preferably comprised in an overall amount of up to 5% by weight, and in particular up to 1% by weight, relative to the total weight of the core.

Preferably, the core of the microcapsule comprises at least 90% by weight, more preferably at least 95% by weight, and in particular at least 99% by weight of cinmethylin, relative to the total weight of the core.

The microparticles comprise a polymeric material which surrounds or embeds cinmethylin. The polymeric material may be any material which is customarily used as wall-forming or matrix-forming material for microparticles. The polymeric material is usually not soluble in water, i.e. its solubility is less then 1 g/l at 25° C. and 1 bar. Preferably, the polymeric material is selected from the group consisting of polyureas, polyurethanes, poly(meth)acrylates, aminoplasts, polystyrenes, polyamides, polysulfonamides, polyesters and polycarbonates.

In case of microcapsules, the polymeric material is the essential part of the shell (also termed wall) which surrounds the cinmethylin-comprising core. In case of matrix particles, the polymeric material is the essential part of the polymer matrix in which cinmethylin is embedded. Suitable polymeric materials for shell and matrix are principally the same and are thus for both forms preferably selected from the group consisting of polyureas, polyurethanes, poly(meth) acrylates, aminoplasts, polystyrenes, polyamides, polysulfonamides, polyesters and polycarbonates.

Polyurea materials are generally prepared by a polymerization process of a suitable polymer wall forming material, such as a polyisocyanate and a polyamine.

"Polyisocyanates" contain two or more isocyanate groups. Polyisocyanates containing two isocyanate groups are also termed diisocyanates. "Polyamines" contain two or more amino groups. Polyamines containing two amino groups are also termed diamines.

Polyurethane materials are generally prepared by a polymerization process of a suitable polymer wall forming material, such as a polyisocyanate and a polyol. "Polyols" contain two or more hydroxyl groups. Polyols containing two hydroxyl groups are also termed diols.

Poly(meth)acrylate materials are generally prepared by a polymerization process of a suitable polymer wall forming material, such as esters of acrylic and/or methacrylic acid, generally $C_1$-$C_{24}$ alkyl esters, acrylic acid and/or methacrylic acid, and optionally also maleic acid and/or other olefinically unsaturated monomers.

Aminoplast materials are generally prepared by a polycondensation process of a suitable polymer wall forming material, generally carbonyl compounds and NH groups containing compounds, and specifically melamin and formaldehyde, or, more often, by curing of a pre-polymer or pre-condensate of these monomers.

Polystyrene materials are generally prepared by a polymerization process of styrene or substituted styrenes and optionally also other olefinically unsaturated monomers.

Polyamide materials are generally prepared by a polymerization process of a suitable polymer wall forming material, such as a polyacid and a polyamine, or lactams. "Polyacids" contain two or more carboxyl groups. Polyacids containing two carboxyl groups are also termed diacids.

Polysulfonamide materials are generally prepared by a polymerization process of a suitable polymer wall forming material, such as a polysulfonic acid and a polyamine. "Polysulfonic acids" contain two or more sulfonic acid groups. Polysulfonic acids containing two sulfonic acid groups are also termed disulfonic acids.

Polyester materials are generally prepared by a polymerization process of a suitable polymer wall forming material, such as a polyacid and a polyol, or lactons.

Polycarbonate materials are generally prepared by a polymerization process of a suitable polymer wall forming material, such as a polycarbonate and a polyol.

Among the above polymeric materials, preference is given to polyureas, poly(meth)acrylates and aminoplasts. For the preparation of microcapsules, more preference is given to polyureas. For the preparation of matrix particles, more preference is given to poly(meth)acrylates and aminoplasts and in particular to poly(meth)acrylates.

Polyurea is a known material for microparticles and in particular a known shell material for microcapsules. In general, polyurea is formed by reacting a polyisocyanate, i.e. a compound having at least two isocyanate groups, with a polyamine, i.e. a compound having at least two amino groups and more precisely a compound having at least two primary and/or secondary amino groups, preferably having two primary amino groups, to form a polyurea wall material. In one embodiment, at least one diisocyanate and at least one diamine having two primary amino groups are used. In another embodiment, either the polyisocyanate or the polyamine or both have more than two reactive —NCO— or NH-groups, respectively. In a further embodiment, the polyurea may be formed by contacting polyisocyanate with water. In this case, first a carbamic acid forms, which immediately decomposes to the corresponding amine and $CO_2$. This amine reacts further with the polyisocyanate to a polyurea. Also, the polyurea can be obtained from a reaction of polyisocyanate with both polyamine and water. Preferably, the polyurea shell contains a polyisocyanate and a polyamine in polycondensed form. Suitable polyisocyanates are known, e.g. from US 2010/0248963 A1, paragraphs [0135] to Suitable polyamines are known, e.g. from US 2010/0248963 A1, paragraphs [0159] to [0169].

Polyisocyanates may be used individually or as mixtures of two or more polyisocyanates. Suitable polyisocyanates are for example aliphatic isocyanates or aromatic isocyanates. These isocyanates may be present as monomeric or oligomeric isocyanates. The NCO content may be determined according to ASTM D 5155-96 A.

The term "aliphatic isocyanates" as used herein also includes cycloaliphatic isocyanates. Examples of suitable aliphatic diisocyanates include tetramethylene diisocyanate, pentamethylene diisocyanate, hexamethylene diisocyanate (H MDI), dodecyl diisocyanate, 1,4-diisocyanato-4-methylpentane, 2-butyl-2-ethylpentamethylene diisocyanate, 2,2,4- or 2,4,4-trimethyl-1,6-hexamethylene diisocyanate, lysine alkyl ester diisocyanate, where alkyl stands for $C_1$-$C_{10}$-alkyl, as well as cycloaliphatic isocyanates such as isophoronediisocyanate (IPDI), 1,4-bisisocyanatocyclohexane, bis-(4-isocyanatocyclohexyl)methane, 2-isocyanatopropylcyclohexyl isocyanate, 3(4)-isocyanatomethyl-1-methylcyclohexyl isocyanate, 2,4'-methylenebis(cyclohexyl) diisocyanate, and 4-methylcyclohexane 1,3-diisocyanate (H-TDI). One example of aliphatic triisocyanates is 4-isocyanatomethyl-1,8-octamethylene diisocyanate.

The term "aromatic isocyanates" as used herein also includes araliphatic isocyanates in which at least one of the isocyanate groups is not bound to the aromatic ring, but to an alkyl group bound in turn to the aromatic ring. Suitable aromatic isocyanates include toluene diisocyanates (TDI), such as 2,4-toluene diisocyanate (2,4-TDI) or 2,6-toluene diisocyanate (2,6-TDI) or mixtures thereof (TDI: a mixture of the 2,4- and 2,6-isomers), triisocyanatotoluene, diphenylmethane-4,4'-diisocyanate (MDI), 2,4'-diphenylmethane diisocyanate (2,4'-MDI), 4,4',4"-triphenylmethane triisocyanate, 2,4,4'-diphenyl ether triisocyanate, 3,3'-dimethyl-4,4'-diphenyl diisocyanate, 3,3'-dimethoxy-4,4'-diphenyl diisocyanate, 1,3- and 1,4-phenylene diisocyanate, diphenyl diisocyanate, 1,5-naphthylene diisocyanate, xylylene diisocyanate or tetramethylxylylene diisocyanate.

Also suitable are oligoisocyanates or polyisocyanates which can be prepared from the abovementioned di- or polyisocyanates or mixtures thereof by means of linking via urethane, allophanate, urea, biuret, uretdione, amide, isocyanurate, carbodiimide, uretonimine, oxadiazinetrione or iminooxadiazinedione structures. Examples are the tetramethylene diisocyanate trimer (i.e. the respective isocyanurate), hexamethylene diisocyanate trimer (i.e. the respective isocyanurate), isophorone diisocyanate trimer (i.e. the respective isocyanurate), polymethylene polyphenyl isocyanate, mixtures of monomeric diphenylmethane diisocyanates and oligomeric diphenylmethane diisocyanates and mixtures of various oligomeric diphenylmethane diisocyanates, optionally also with monomeric diphenylmethane diisocyanates (polymeric MDI). The oligomeric or polymeric isocyanates have an average functionality which is generally in the range of 2.0 to 4.0, preferably 2.1 to 3.2, and more preferably 2.3 to 3.0. Typically, these oligomeric isocyanates have a viscosity (determined according to DIN 53018; 25° C.) in the range from 20 to 1000 mPas, more preferably from 80 to 500 mPas and especially from 150 to 320 mPas. Such oligomeric isocyanates are commercially available, for example from BASF SE under the tradenames Lupranat® M5, Lupranat® M 10, Lupranat® M20, Lupranat® M50, Lupranat® M70, Lupranat® M200, Lupranat® M 103 or under the tradename Basonat® A270.

Also suitable are mixtures of the abovementioned di- or polyisocyanates with oligoisocyanates or polyisocyanates.

It is also possible to use masked (blocked) di- or polyisocyanates. In masked or blocked di- or polyisocyanates the isocyanate groups are reacted reversibly to form another functional group that under appropriate conditions can be converted back into the isocyanate group. Preferably the isocyanate group is reacted with an alcohol, preferably a monoalcohol, to form a urethane group. The alcohol is generally eliminated simply during the reaction of the blocked di- or polyisocyanate with the polyamine. Blocking the isocyanate groups lowers the very high reactivity of the isocyanates and enables controlled reaction with the polyamine and hence controlled construction of polyureas.

Also suitable are adducts of diisocyanates with polyhydric alcohols, such as ethylene glycol, glycerol and trimethylolpropane, obtained by addition, per mole of polyhydric alcohol, of a number of moles of diisocyanate corresponding to the number of hydroxyl groups of the respective alcohol and mixtures thereof with the aforementioned diisocyanates. In this way, several molecules of diisocyanate are linked through urethane groups to the polyhydric alcohol to form high molecular weight polyisocyanates. A particularly suitable product of this kind, DESMODUR® L (Bayer Corp., Pittsburgh), can be prepared by reacting three moles of toluene diisocyanate with one mole of 2-ethylglycerol (1,1-bismethylolpropane). Further suitable products are obtained by addition of hexamethylene diisocyanate or isophorone diisocyanate with ethylene glycol or glycerol.

Preferred polyisocyanates are the above-mentioned aliphatic diisocyanates, in particular hexamethylene diisocyanate or isophorone diisocyanate, further diphenylmethane-4,4'-diisocyanate, toluene diisocyanates, and oligomeric isocyanates, in particular trimers (isocyanurates) of the above-mentioned aliphatic diisocyanates. Specifically, hexamethylene diisocyanate or its trimer, and very specifically hexamethylene diisocyanate trimer is used.

Suitable polyamines within the scope of this invention will be understood as meaning in general those compounds that contain two and more amino groups in the molecule, which amino groups may be linked to aliphatic or aromatic moieties.

The term "aliphatic polyamines" as used herein includes cycloaliphatic amines. Examples of suitable aliphatic polyamines are $\alpha,\omega$-diamines of the formula $H_2N-(CH_2)_p-NH_2$, wherein p is an integer from 2 to 6. Exemplary of such diamines are ethylene diamine, propylene-1,3-diamine, tetramethylene diamine, pentamethylene diamine and hexamethylene diamine. A preferred diamine is hexamethylene diamine. Further suitable aliphatic polyamines are polyethylenimines of the formula $H_2N-(CH_2-CH_2-NH)_q-H$, wherein q is an integer from 2 to 20, preferably 3 to 5. Representative examples of such polyethylenimines are diethylene triamine, triethylene tetramine, tetraethylene pentamine and pentaethylene hexamine. Further suitable aliphatic polyamines are dioxaalkane-$\alpha,\omega$-diamines, such as 4,9-dioxadodecane-1,12-diamine of the formula $H_2N-(CH_2)_3O-(CH_2)_4O-(CH_2)_3-NH_2$. Further suitable aliphatic polyamines are amines carrying 3 aminoalkyl groups. Examples are tris(2-aminoethyl)amine, tris(2-aminopropyl)amine, tris(3-aminopropyl)amine, tris(2-aminobutyl)amine, tris(3-aminobutyl)amine, tris(4-aminobutyl)amine, tris(5-aminopentyl)amine and tris(6-aminohexyl)amine. Further suitable aliphatic polyamines are cycloaliphatic diamines, such as isophorone diamine, diaminodicyclohexylmethane or bis(aminomethyl)-cyclohexane.

Examples of suitable aromatic polyamines are 1,3-phenylene diamine, 2,4- and 2,6-toluene diamine, 4,4'-diaminodiphenyl methane, 1,5-diaminonaphthalene, 1,3,5-triaminobenzene, 2,4,6-triaminotoluene, 1,3,6-triaminonaphthalene, 2,4,4'-triaminodiphenyl ether, 3,4,5-triamino-1,2,4-triazole and 1,4,5,8-tetraamino-anthraquinone.

Those polyamines which are insoluble or insufficiently soluble in water may be used as their hydrochloride salts.

The polyamines may be used individually or as mixtures of two or more polyamines. Preferred polyamines are aliphatic diamines, in particular the above-mentioned $\alpha,\omega$-diamines. Specifically, hexamethylene diamine is used.

The relative amount of each complementary wall-forming component will vary with their equivalent weights. In general, approximately stoichiometric amounts are preferred, while an excess of one component may also be employed, especially an excess of polyisocyanate. The total amount of wall-forming components approximately corresponds to the total amount of polymeric wall-forming materials.

Microcapsules containing a polyurea shell are preferably prepared by an interfacial polymerization process of a suitable polymer wall forming material, such as a polyisocyanate and a polyamine. Interfacial polymerization is usually performed in an aqueous oil-in-water emulsion or suspension of the core material containing dissolved therein at least one part of the polymer wall forming material. During the polymerization, the polymer segregates from the core material to the boundary surface between the core material and water thereby forming the wall of the microcapsule. Thereby an aqueous suspension of the microcapsule material is obtained. Further details are given below in context with the method of the present invention. Poly(meth)acrylate is also a known material for microparticles, both in form of microcapsules and matrix particles, for example from WO 2008/071649, EP 0 457154 or DE 10 2007 055 813. Usually, the poly(meth)acrylate comprises $C_1$-$C_{24}$ alkyl esters of acrylic and/or methacrylic acid, acrylic acid, methacrylic acid, and/or maleic acid in polymerized form. More preferably, the poly(meth)acrylate comprises methyl methacrylate and methacrylic acid. The poly(meth)acrylate may also comprise in polymerized form one or more difunctional or polyfunctional monomers. The poly(meth)acrylate may further comprise other monomers.

Unless specified otherwise, the terms "acrylate" and "methacrylate" relate to the esters of acrylic acid and methacrylic acid, respectively. "Poly(meth)acrylate" relates to polymers of acrylates, polymers of methacrylates, mixtures of polymers of acrylates and polymers of methacrylates and to copolymers of acrylates and methacrylates. The polymers may moreover comprise other ethylenically unsaturated monomers in polymerized form.

More preferably, the poly(meth)acrylate polymer is synthesized from 30 to 100% by weight, based on the total weight of the monomers, of one or more monomers (monomers 1) selected from the group consisting of $C_1$-$C_{24}$ alkyl esters of acrylic and/or methacrylic acid, acrylic acid, methacrylic acid, and maleic acid, 10 to 70% by weight, based on the total weight of the monomers, of one or more difunctional or polyfunctional monomers (monomers II), and 0 to 40% by weight, based on the total weight of the monomers, of one or more other monomers (monomers ill).

The poly(meth)acrylate of the capsule wall comprise generally at least 30%, in a preferred form at least 40%, in a particularly preferred form at least 50%, more particularly at least 60%, with very particular preference at least 70%, and also up to 100%, preferably not more than 90%, more particularly not more than 85%, and, with very particular preference, not more than 80%, by weight, of at least one monomer selected from the group consisting of $C_1$-$C_{24}$ alkyl esters of acrylic and/or methacrylic acid, acrylic acid, methacrylic acid, and maleic acid (monomers 1), in copolymerized form, based on the total weight of the monomers.

Furthermore the poly(meth)acrylate of the capsule wall comprises preferably at least 10%, preferably at least 15%, preferentially at least 20%, and also, in general, not more than 70%, preferably not more than 60%, and with particular preference not more than 50%, by weight, of one or more difunctional or polyfunctional monomers (monomers ii), in copolymerized form, based on the total weight of the monomers. In another preferred embodiment, the poly(meth)acrylate of the capsule wall comprises preferably at least 10%, preferably at least 15%, and also, in general, not more than 50%, preferably not more than 40% by weight, of one or more polyfunctional monomers (monomers II), in copolymerized form, based on the total weight of the monomers.

Additionally, the poly(meth)acrylate may comprise up to 40%, preferably up to 30%, more particularly up to 20%, by weight, of other monomers III, in copolymerized form. Preferably however, the capsule wall is synthesized only from monomers of groups I and II.

Suitable monomers I are $C_1$-$C_{24}$ alkyl esters of acrylic and/or methacrylic acid and also the unsaturated $C_3$- and $C_4$-carboxylic acids such as acrylic acid, methacrylic acid, and also maleic acid. Suitable monomers I are isopropyl, isobutyl, sec-butyl, and tert-butyl acrylates and the corresponding methacrylates, and also, with particular preference, methyl, ethyl, n-propyl, and n-butyl acrylates and the corresponding methacrylates. In general the methacrylates and methacrylic acid are preferred.

According to one preferred embodiment the microcapsule walls comprise 25% to 75% by weight of maleic acid, methacrylic acid and/or acrylic acid, more particularly methacrylic acid, based on the total amount of the monomers I, in copolymerized form.

Suitable monomers II are difunctional or polyfunctional monomers. By difunctional or polyfunctional monomers are meant compounds which have at least two nonconjugated ethylenic double bonds. Contemplated primarily are divinyl monomers and polyvinyl monomers. They bring about crosslinking of the capsule wall during the polymerization. In another preferred embodiment, suitable monomers II are polyfunctional monomers.

Suitable divinyl monomers are divinylbenzene and divinylcyclohexane. Preferred divinyl monomers are the diesters of diols with acrylic acid or methacrylic acid, and also the diallyl and divinyl ethers of these diols. Mention may be made, by way of example, of ethanediol diacrylate, ethylene glycol dimethacrylate, 1,3-butylene glycol dimethacrylate, methallylmethacrylamide, allyl acrylate, and allyl methacrylate. Particular preference is given to propanediol, 1,4-butanediol, pentanediol, and hexanediol diacrylates and the corresponding methacrylates.

Preferred polyvinyl monomers are the polyesters of polyols with acrylic acid and/or methacrylic acid, and also the polyallyl and polyvinyl ethers of these polyols, trivinylbenzene and trivinylcyclohexane. Particular preference is given to trimethylolpropane triacrylate and trimethacrylate, pentaerythritol triallyl ether, pentaerythritol tetraallyl ether, pentaerythritol triacrylate, and pentaerythritol tetraacrylate, and also their technical mixtures.

Monomers III contemplated are monomers different from the monomers I and II, such as vinyl acetate, vinyl propionate, vinylpyridine, and styrene or α-methylstyrene. Particular preference is given to itaconic acid, vinylphosphonic acid, maleic anhydride, 2-hydroxyethyl acrylate and methacrylate, acrylamide-2-methylpropanesulfonic acid, methacrylonitrile, acrylonitrile, methacrylamide, N-vinylpyrrolidone, N-methylolacrylamide, N-methylolmethacrylamide, dimethylaminoethyl methacrylate, and diethyl-aminoethyl methacrylate.

Aminoplast polymers, which are also termed amino resins, amino condensation resins or amido resins, are also a known material for microparticles, both in form of microcapsules and matrix particles. Aminoplasts are polycondensation products of one or more aldehydes, such as formaldehyde, acetaldehyde, propanal, glyoxal or glutaraldehyde, with one or more amino compounds having usually at least two primary amino groups, such as urea, thiourea, melamine, which may be wholly or partially etherified, cyanoguanamine (=dicyandiamide) and benzoguanamine. Examples of aminoplast polymers are polycondensates of melamine and formaldehyde (melamine-formaldehyde resins or MF resins), including resins derived from wholly or partially etherified melamine-formaldehyde condensates, urea-formaldehyde resins (UF resins), thiourea-formaldehyde resins (TUF resins), polycondensates of melamine, urea and formaldehyde (MUF resins), including resins derived from wholly or partially etherified melamine-urea-formaldehyde condensates, polycondensates of melamine, thiourea and formaldehyde (MTUF resins, including resins derived from wholly or partially etherified melamine-thiourea-formaldehyde condensates, urea-glutaraldehyde resins, benzoguanamine-formaldehyde polycondensates, dicyandiamide formaldehyde polycondensates and urea-glyoxal polycondensates. Suitable aminoplast polymers for microencapsulation are known and can be found, inter alia, in Kirk-Othmer, Encyclopedia of Chemical Technology, 3rd edition, Vol. 2, pp. 440-469, the prior art cited in the introductory part, U.S. Pat. No. 4,918,317, EP 26914, EP 218887, EP 319337, EP 383,337, EP 415273, DE 19833347, DE 19835114 and WO 01/51197.

In UF and TUF resins, the molar ratios of urea or thiourea to formaldehyde are generally in the range from 1:0.8 to 1:4, in particular from 1:1.5 to 1:4, especially from 1:2 to 1:3.5. If glutaraldehyde is used instead of formaldehyde, the molar ratios of urea or thiourea to glutaraldehyde may in particular be in the range from 1:1.2 to 1:3, especially in the range from 1:1.5 to 1:2.5.

In MF and MUF resins, the molar ratios of melamine to formaldehyde are generally in the range from 1:1.5 to 1:10, in particular from 1:3 to 1:8 preferably 1:4 to 1:6.

In MUF and MTUF resins, the molar ratios of melamine+ urea or thiourea to formaldehyde are generally in the range from 1:0.8 to 1:9, in particular from 1:2 to 1:8 preferably 1:3 to 1:6. The molar ratio of urea or thiourea to melamine may be in the range from 50:1 to 1:100 and in particular from 30:1 to 1:30.

In the preparation of the aforementioned aminoplast resins, the pre-condensates may be used in the form of etherified pre-condensates of amino compound and aldehyde. In these etherified pre-condensates the methylol groups formed by the reaction of the amino groups with formaldehyde with an alkanol or an alkandiol, in particular with a $C_1$-$C_4$-alkanol, such as methanol, ethanol, n-propanol or n-butanol, in particular methanol, or a $C_2$-$C_4$-alkandiol, such as ethylene glycol. The degree of etherification of these resins can be adjusted by the molar ratio of amino groups to alkanol which is typically in the range from 10:1 to 1:10, preferably in the range from 2:1 to 1:5.

The aminoplast polymer material, which surrounds or embeds the core, is preferably selected from the group consisting of melamine-formaldehyde resins, including melamine-formaldehyde resins derived from wholly or partially etherified melamine-formaldehyde condensates, and urea-formaldehyde resins and mixtures thereof. Especially, the aminoplast polymer material which surrounds or embeds the core is a melamine-formaldehyde resin, in particular a melamine-formaldehyde resin which is derived from wholly or partially etherified melamine-formaldehyde condensates, which may contain small amount, e.g. 1 to 20 mol.-%, based on melamine, of urea.

As already said, for the preparation of microcapsules, particular preference is given to polyureas. Suitable polyureas are described above. Among these, preference is given to polyureas prepared from
- at least one polyisocyanate selected from the group consisting of the above-mentioned aliphatic diisocyanates, aromatic diisocyanates, oligomeric isocyanates, in particular trimers (isocyanurates) of the above-mentioned aliphatic diisocyanates, and mixtures thereof; and
- at least one polyamine selected from the group consisting of the above-mentioned aliphatic diamines and mixtures thereof.

More preference is given to polyureas prepared from
- at least one polyisocyanate selected from the group consisting of hexamethylene diisocyanate, isophorone diisocyanate; diphenylmethane-4,4'-diisocyanate, the toluene diisocyanates, oligomeric isocyanates, in particular trimers (isocyanurates) of the above-mentioned aliphatic diisocyanates, and mixtures thereof; and
- at least one polyamine selected from the group consisting of the above-mentioned α,ω-diamines.

In particular, the polyureas are prepared from
- at least one polyisocyanate selected from the group consisting of hexamethylene diisocyanate, its trimer and mixtures thereof, and
- hexamethylene diamine.

In microcapsules, the weight ratio of cinmethylin and the polymeric material comprised in the shell is preferably of from 1:1 to 80:1, more preferably from 4:1 to 40:1, in particular from 8:1 to 25:1.

As the shell often consists essentially of the polymeric material, i.e. to at least 95% by weight, based on the total weight of the shell, alternatively expressed, the weight ratio of cinmethylin and the shell is preferably of from 1:1 to 80:1, more preferably from 4:1 to 40:1, in particular from 8:1 to 25:1.

In matrix particles the weight ratio of cinmethylin and the polymeric material forming the polymer matrix is preferably of from 10:1 to 1:10, more preferably from 5:1 to 1:5, and in particular from 3:1 to 1:4.

Whether microcapsules or rather matrix particles are formed depends i.a. on the polymerization conditions under which the monomers on which the polymeric material is based are reacted. The required conditions are known to those skilled in the art. For instance, a typical process for obtaining core/shell microcapsules is the above-mentioned interfacial polymerization process in an aqueous oil-in-water emulsion or suspension, where the core material containing dissolved therein at least one part of the polymer wall forming material is used as a starting material. As said, during polymerization, the polymer segregates from the core material to the boundary surface between the core material and water thereby forming the wall of the microcapsule. Matrix particles are for example obtained when applying a miniemulsion polymerization process using high shear forces and sufficient amounts of emulsifiers for finely dispersing the starting materials (i.e. compound to be embedded—here cinmethylin—and monomers for forming the polymer matrix) in an aqueous medium. This process is especially suitable for obtaining matrix particles with a poly(meth)acrylate matrix.

The composition of the invention contains the microparticles in an amount of preferably from 10 to 70% by weight, more preferably from 20 to 60% by weight, even more preferably from 30 to 50% by weight, in particular from 35 to 50% by weight, based on the total weight of the composition.

The composition of the invention contains cinmethylin in an amount of preferably from 10 to 70% by weight, more preferably from 20 to 60% by weight, even more preferably from 30 to 50% by weight, and in particular from 35 to 45% by weight, based on the total weight of the composition.

The composition of the invention is preferably a liquid composition at 20° C. More preferably, the composition is an aqueous dispersion. In the aqueous dispersion water or an aqueous medium is usually the continuous phase, while the microparticles and also the at least one herbicide different from cinmethylin, if this is not soluble in the continuous phase, form the disperse phase.

The "aqueous medium" comprises an aqueous solvent and optionally compounds dissolved therein, e.g. surfactants as mentioned below or other conventional formulation additives, such as thickeners or biocides; see also below. The aqueous solvent in the aqueous medium is either water or a mixture of water with a water-miscible organic solvent, such as $C_1$-$C_4$-alkanols, e.g. methanol, ethanol, n-propanol, isopropanol, n-butanol, 2-butanol, isobutanol, or tert-butanol, $C_2$-$C_5$-alkanediols and $C_3$-$C_8$-alkanetriols, which are preferably selected from the group consisting of ethylene glycol, 1,2-propanediol, 1,3-propanediol, glycerol and 1,4-butanediol. If the aqueous solvent is a mixture of water and the aforementioned water-miscible organic solvent, the weight ratio of water to water-miscible organic solvent in the aqueous solvent is preferably in the range of from 99:1 to 1:1; more preferably in the range of from 50:1 to 3:1; and most preferably in the range of from 20:1 to 4:1. Expressed differently, the amount of organic solvent may be from 1 to 50% by weight, more preferably from 2 to 25% by weight, and most preferably from 5 to 20% by weight, based on the total weight of the aqueous solvent. In a particular embodiment, the aqueous solvent consists essentially of water, which means that water makes up for at least 96% by weight, preferably at least 98% by weight of the aqueous solvent.

The aqueous dispersion comprises preferably at least 15% by weight, more preferably at least 25% by weight, and in particular at least 35% by weight of water, based on the total weight of the dispersion.

In particular, the composition of the invention is a suspension concentrate.

The composition of the invention may comprise at least one further auxiliary. Suitable auxiliaries are for example: surfactants, further dispersants, e.g. inorganic dispersants, emulsifiers, wetting agents, further adjuvants, inorganic salts, solubilizers, penetration enhancers, protective colloids, adhesion agents, thickeners, humectants, antifoams, antifreeze agents, stabilizers, antimicrobial agents, pigments, colorants, buffers. Among these, preference is given to surfactants, further dispersants, wetting agents, thickeners, antifoams, antifreeze agents, antimicrobial agents and buffers.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

In a particular embodiment, the composition of the invention does not contain any vinylpyrrolidone co- or terpolymer emulsifier/dispersant/surfactant and especially does not contain the vinylpyrrolidone co- or terpolymer emulsifiers used in WO 94/213139.

The composition may comprise a sulfonate dispersant selected from lignosulfonate, naphthalene sulfonate formaldehyde condensate, or mixtures thereof. Preferably, the sulfonate dispersant is selected from lignosulfonate or mixtures of lignosulfonate and naphthalene sulfonate formaldehyde condensate. In particular, the sulfonate dispersant is lignosulfonate.

Lignosulfonates are known and are defined, for example, in Roempp's dictionary of chemistry, 9th Edition, volume 3, Georg-Thieme Verlag, Stuttgart, N.Y. 1990, page 2511. Lignosulfonates which are suitable are the alkali metal salts and/or alkaline earth metal salts and/or ammonium salts, for example the ammonium, sodium, potassium, calcium or magnesium salts of lignosulfonic acid. The sodium, potassium and/or calcium salts are preferably used. Naturally, the term lignosulfonates also encompasses mixed salts of different ions, such as potassium/sodium lignosulfonate, potassium/calcium lignosulfonate and the like, in particular sodium/calcium lignosulfonate. The molecular mass of the lignosulfonate may vary from 500 to 200,000 Da. Preferably, the lignosulfonate has a molecular weight of 700 to 50,000 Da, more preferably from 900 to 20,000 Da, and in particular from 1000 to 10,000 Da, specifically from 1000 to 5000 Da. The lignosulfonate is usually soluble in water (e.g. at 20° C.), e.g. at least 5% by weight, preferably at least 10% by weight, and in particular at least 20% by weight.

Naphthalene sulfonate formaldehyde condensates are oligomers obtainable by reaction (e.g. polycondensation) of naphthalene sulfonate and formaldehyde. The naphthalene sulfonate formaldehyde condensates has usually a molecular mass of 300 to 10,000 Da, preferably of 500 to 5000 Da, and in particular of 500 to 2500 Da. The naphthalene group may optionally substituted by a linear or branched $C_1$-$C_8$ alkyl. The naphthalene sulfonate formaldehyde condensates is usually soluble in water (e.g. at 20° C.), e.g. at least 5% by weight, preferably at least 10% by weight, and in particular at least 20% by weight. Naphthalene sulfonate formaldehyde condensates which are suitable are the alkali metal salts and/or alkaline earth metal salts and/or ammonium salts, for example the ammonium, sodium, potassium, calcium or magnesium salts of lignosulfonic acid. The sodium, potassium or calcium salts are preferably used, the sodium, potassium and/or calcium salts are very particularly preferably used.

The composition may comprise from 0.05 to 15% by weight, preferably from 0.1 to 5% by weight, more preferably from 0.3 to 3% by weight and in particular from 0.5 to 2.0% by weight of the sulfonate dispersant (e.g. the lignosulfonate).

Suitable nonionic surfactants are alkoxylate surfactants. N-substituted fatty acid amides, amine oxides, esters, sugar-based surfactants, polymeric surfactants, and mixtures thereof. Examples of alkoxylate surfactants are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are homo- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines.

Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable further adjuvants are compounds which have a neglectable or even no herbicidal activity themselves, and which improve the biological performance of the herbicides on the target. Examples are surfactants, mineral or vegetable oils, and other auxilaries. Further examples are listed by Knowles, Adjuvants and additives, Agrow Reports DS256, T&F Informa UK, 2006, chapter 5.

Further dispersants are for example inorganic dispersants. Suitable inorganic dispersants, also termed anticaking agents, are useful for preventing agglutination of the microparticles, and are for example silica (such as, for example Sipernat® 22 from Degussa), alumina, calcium carbonate and the like, among which silica is preferred. The concentration of inorganic dispersants in the composition of the invention will generally not exceed 2% by weight, based on the total weight of the final suspension, and, if present, it is preferably in the range from 0.01 to 2% by weight, in particular from 0.02 to 1.5% by weight and especially from 0.1 to 1% by weight, based on the total weight of the composition.

Suitable inorganic salts are water-soluble and are for example selected from sulfates, chlorides, nitrates, mono and dihydrogen phosphates of alkali metals, the sulfates, chlorides, nitrates, mono and dihydrogen phosphates of ammonia, chlorides and nitrates of alkaline earth metals and magnesium sulfate. Examples include lithium chloride, sodium chloride, potassium chloride, lithium nitrate, sodium nitrate, potassium nitrate, lithium sulfate, sodium sulfate, potassium sulfate, sodium monohydrogen phosphate, potassium monohydrogen phosphate, sodium dihydrogen phosphate, potassium dihydrogen phosphate, magnesium chloride, calcium chloride, magnesium nitrate, calcium nitrate, magnesium sulfate, ammonium chloride, ammonium sulfate, ammonium monohydrogen phosphate, ammonium dihydrogen phosphate and the like. Preferred inorganic salts are sodium chloride, potassium chloride, calcium chloride, ammonium sulfate and magnesium sulfate with ammonium sulfate and magnesium sulfate being especially preferred.

The composition may contain the water-soluble inorganic salt in an amount of from 1 to 200 g/L, preferably from 2 to 150 g/L and especially from 10 to 130 g/L. Water-solubility of the salt means solubility in water of at least 50 g/L, in particular at least 100 g/L or even at least 200 g/L at 20° C.

In another embodiment, the composition does not contain or contains less than 10 g/L, in particular less than 1 g/L of the water-soluble inorganic salt.

Protective colloids are for example polyvinylalcohols, starch, cellulose derivatives or copolymers containing vinylpyrrolidone.

Suitable thickeners are compounds which affect the flow behavior of composition of the invention, especially if this is an aqueous dispersion, e.g. a suspension concentrate, and may assist in stabilizing the aqueous suspension of the microparticles against caking. Mention may be made, in this connection, for example, of commercial thickeners based on polysaccharides, such as methylcellulose, carboxymethylcellulose, hydroxypropylcellulose (Klucel® grades), Xanthan Gum (commercially available e.g. as Kelzan® grades from Kelco or Rhodopol® grades from Rhodia), synthetic polymers, such as acrylic acid polymers (Carbopol® grades), polyvinyl alcohol (e.g. Mowiol® and Poval® grades from Kuraray), polyvinyl pyrrolones, polycarboxylates, polyethers or isocyanate-linked polyethers, silicic acid or phyllosilicates, such as montmorillonite and bentonites, which may be hydrophobized, (commercially available as Attaclay® grades and Attaflow® grades from BASF SE; or as Veegum® grades and Van Gel® grades from R.T. Vanderbilt). In the context of the present invention, Xanthan Gum is a preferred thickener. The concentration of thickeners in the aqueous suspension will generally not exceed 2% by weight, based on the total weight of the aqueous suspension, and is preferably in the range from 0.01 to 2% by weight, in particular from 0.02 to 1.5% by weight and especially from 0.1 to 1% by weight, based on the total weight of the aqueous suspension or the final formulation, respectively.

Suitable antimicrobial agents (preservatives) to prevent microbial spoiling of the compositions of the invention include formaldehyde, alkyl esters of p-hydroxybenzoic acid, sodium benzoate, 2-bromo-2-nitropropane-1,3-diol (bronopol), o-phenylphenol, isothiazolinones, such as benzisothiazolinone or alkylisothiazolinones, e.g. 5-chloro-2-methyl-4-isothiazolinone, pentachlorophenol, 2,4-dichlorobenzyl alcohol and mixtures thereof. Commercially available preservatives that are based on isothiazolinones are for example marketed under the trademarks Proxel® (Arch Chemical), Acticide® MBS (Thor Chemie) and Kathon® MK (Rohm & Haas).

Suitable anti-freezing agents are ethylene glycol, propylene glycol, urea and glycerin.

Antifoam agents suitable for the compositions according to the invention are, for example, silicones, especially silicone emulsions (such as, for example, Silicone SRE-PFL from Wacker or Rhodorsil® from Bluestar Silicones), polysiloxanes and modified polysiloxanes including polysiloxane blockpolymers such as FoamStar® SI and FoamStar® ST products of BASF SE, long-chain alcohols, fatty acids, salts of fatty acids, organofluorine compounds and mixtures thereof.

Suitable pigments and colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

If appropriate, the composition according to the invention, in particular if this is an aqueous dispersion, may comprise buffers to regulate the pH. Examples of buffers are alkali metal salts of weak inorganic or organic acids such as, for example, phosphoric acid, boric acid, acetic acid, propionic acid, citric acid, fumaric acid, tartaric acid, oxalic acid and succinic acid.

Suitable tackifiers or binders are polyvinylpyrrolidons, polyvinylacetates, polyvinyl alcohols, polyacrylates, biological or synthetic waxes, and cellulose ethers.

The composition generally comprises the auxiliaries in an overall amount of at most 15% by weight, preferably at most 10% by weight, based on the total weight of the composition.

The composition of the invention can be prepared by providing microparticles containing cinmethylin and a polymeric material which surrounds or embeds cinmethylin, and mixing these microparticles with the further herbicide(s).

The cinmethylin-containing microparticles can principally be prepared by any method known in the art for preparing microparticles. In particular, the microparticles are prepared by polymerizing the monomers from which the polymeric material, i.e. the polymeric shell (in case of microcapsules) or polymer matrix (in case of matrix particles) is to be formed, or polymerizing or curing a pre-polymer or pre-condensate from which the polymeric material, i.e. the polymeric shell (in case of microcapsules) or polymer matrix (in case of matrix particles) is to be formed, in the presence of cinmethylin.

Thus, the present invention relates to a method for preparing the composition of the invention, comprising polymerizing one or more monomers from which the polymeric material comprised in the microparticles, i.e. in the shell (in case of microcapsules) or polymer matrix (in case of matrix particles) is to be formed or curing a pre-polymer or pre-condensate from which the polymeric material comprised in microparticles, i.e. in the shell (in case of microcapsules) or polymer matrix (in case of matrix particles) is to be formed, in the presence of cinmethylin, and mixing the resulting cinmethylin-containing microparticles with the at least one herbicide different from cinmethylin.

The formation of microparticles via polymerization of suitable monomers in the presence of the core or embedded material, here cinmethylin, is principally known. The optimum method depends i.a. on the intended polymeric material and particle form (e.g. core/shell capsule or matrix particle).

Suitable and preferred monomers for forming various shell or matrix materials have already been described above. Pre-polymers or pre-condensates are generally used for preparing an aminoplast shell or matrix. Suitable aminoplast pre-polymers are described above and below.

For preparing a composition which is an aqueous dispersion, e.g. a suspension concentrate, the polymerization of the monomers or of the pre-polymer is often carried out in the presence of cinmethylin and also of water.

As already explained above, microcapsules containing a polyurea shell are preferably prepared by an interfacial polymerization process of a suitable polymer wall forming material, such as a polyisocyanate and a polyamine. Interfacial polymerization is usually performed in an aqueous oil-in-water emulsion or suspension of the core material containing dissolved therein at least one part of the polymer wall forming material. During the polymerization, the polymer segregates from the core material to the boundary surface between the core material and water thereby forming the wall of the microcapsule. Thereby an aqueous suspension of the microcapsule material is obtained.

Polyisocyanates react rather fast with water, yielding carbamic acid, which, due to its instability, decomposes into the corresponding amine and $CO_2$. If this reaction is not desired, and the polyisocyanate is intended to react essentially only with the polyamine, it is expedient to avoid any essential contact of the polyisocyanate with water. For this purpose, in a preferred embodiment, cinmethylin and the polyisocyanate are first mixed. Preferably, cinmethylin is used in excess, the weight ratio of cinmethylin to the polyisocyanate being preferably of from 2:1 to 160:1, more preferably from 4:1 to 80:1, in particular from 8:1 to 50:1, e.g. from 15:1 to 25:1. In this mixture the polyisocyanate is sufficiently protected from hydrolysis. If desired, the mixture can also contain one or more organic solvents, suitably organic solvents which are not miscible with water. Suitable water-immiscible organic solvents are described above.

The resulting mixture is then mixed with water and optionally also with one or more of the above-described auxiliaries. Mixing with water generally includes a step of high speed or high sheer mixing, which can be carried out with any high speed or high shear mixer known in the art. Suitable mixing devices include in particular high shear mixers, such as Ultra-Turrax apparatus, static mixers, e.g. systems having mixing nozzles, agitator bead mills, colloid mills, cone mills and other homogenizers. Ultra Turrax have suitably fast rotation speed, such as at least 5000 rpm, preferably at least 7000 rpm and in particular at least 10000 rpm.

This is preferably followed by admixture with the polyamine. Preferably the polyamine is added to the aqueous mixture, either as such or dissolved or dispersed in water.

The reaction temperature is not very critical and can range, e.g., from 15 to 90° C., in particular from 20 to 90° C. If the monomers are less reactive, elevated reaction temperatures are expedient, such as 30 to 90° C. or 50 to 80° C.

If desired, one or more of the above-described auxiliaries can be added during the reaction or after its completion.

Finally, the at least one further herbicide different from cinmethylin is added. If desired, one or more of the above-described auxiliaries can be added together with the at least one further herbicide or after its addition.

Compositions containing microcapsules the shell material of which is a polyurethane can be prepared in a similar manner, where of course a polyol is added instead of a diamine.

The microcapsules with a poly(meth)acrylate shell are generally obtainable via in situ polymerization. An oil-in-water emulsion is prepared from the monomers, cinmethylin and suitably also a protective colloid. Polymerization of the monomers is then triggered by addition of a free radical starter and optionally also by heating and if appropriate controlled through a further temperature increase. The resulting polymers form the capsule wall which surrounds the core substance. This general principle is described for example in WO 2008/071649 or DE-A-10 139 171.

Microcapsules with a polystyrene shell can be prepared analogously.

Microcapsules with aminoplast shells are preferably prepared by polymerizing or curing an aminoplast pre-polymer (pre-condensate) in the presence of cinmethylin. Suitable pre-condensates include pre-condensates of melamine and formaldehyde, including wholly or partially etherified melamine-formaldehyde pre-condensates, urea-formaldehyde pre-condensates, thiourea-formaldehyde pre-condensates, pre-condensates of melamine, urea and formaldehyde (MUF resins), including mixtures of wholly or partially etherified melamine-formaldehyde pre-condensates and urea-formaldehyde pre-condensates, pre-condensates of urea and glutaraldehyde, pre-condensates of benzoguanamine and formaldehyde, mixtures of dicyandiamide and formaldehyde and urea-glyoxal polycondensates. Suitable aminoplast pre-condensates for microencapsulation are known and can be found, inter alia, in Kirk-Othmer, Encyclopedia of Chemical Technology, 3rd edition, Vol. 2, pp. 440-469, the prior art cited in the introductory part, U.S. Pat. No. 4,918,317, EP 26914, EP 218887, EP 319337, EP 383,337, EP 415273, DE 19833347, DE 19835114 and WO 01/51197. Suitable pre-condensates are commercially available, e. g. Cymel types, such as but not limited to Cymel® 303, 327, 328 or 385 (etherified melamine formaldehyde resins of Cytec), Maprenal® types, such as but not limited to Maprenal® MF 900w/95, MF 915/751B, MF 920/75WA, MF 921w/85WA, (etherified melamine formaldehyde resins of ineos), Kauramin® types of BASF SE, such as but not limited to Kauramin® 783, Kauramin® 792 or Kauramin® 753 (melamine formaldehyde resins), Kauramin® 620 or Kauramin® 621 (melamine urea formaldehyde resins), Kaurit® types of BASF SE, such as but not limited to Kaurit® 210, 216, 217 or 220 (urea formaldehyde resins), Luracoll® types such as Luracoll® SD (etherified melamine formaldehyde resins), Luwipal® types such as but not limited to Luwipal® 063, Luwipal® 069 (etherified melamine formaldehyde resins), or Plastopal® types such as but not limited to Plastopal® BTM, Plastopal® BTW (etherified urea formaldehyde resins). The pre-condensates may be used in the form of etherified pre-condensates of amino compound and aldehyde. In these etherified pre-condensates the methylol groups formed by the reaction of the amino groups with formaldehyde with an alkanol or an alkandiol, in particular with a $C_1$-$C_4$-alkanol, such as methanol, ethanol, n-propanol or n-butanol, in particular methanol, or a $C_2$-$C_4$-alkandiol, such as ethylene glycol. The degree of etherification of these resins can be adjusted by the molar ratio of amino groups to alkanol which is typically in the range from 10:1 to 1:10, preferably in the range from 2:1 to 1:5.

The pre-condensates are preferably selected from the group consisting of melamine-formaldehyde resins, including wholly or partially etherified melamine-formaldehyde pre-condensates, and urea-formaldehyde pre-condensates and mixtures thereof. Especially, the pre-condensate is a wholly or partially etherified melamine-formaldehyde condensate, which may contain small amounts, e.g. 1 to 20 mol.-%, based on melamine, of urea.

For the preparation of microcapsules with an aminoplast shell, generally an aqueous dispersion containing cinmethylin and the pre-condensate is prepared. Preferably, suitable mixing devices, such as stirrers or inline-mixers are used in order to achieve a uniform distribution of the pre-condensate in the aqueous dispersion. It may be beneficial to add the pre-condensate, preferably in the form of a solution, to an aqueous dispersion of cinmethylin with stirring. Preferably, the addition of the pre-condensate is performed under conditions where the polycondensation reaction is slow or does not occur, e.g. where either the pH of the aqueous suspension at least pH 6, e.g. in the range form pH 6 to pH 10, or where the temperature does not exceed 30° C. or both.

The polycondensation of the aminoplast pre-condensate can be effected or initiated in a well-known manner, e.g. by heating the aqueous dispersion to a certain reaction temperature, at a pH, where the polycondensation at the reaction temperature occurs. During the polycondensation, the aminoplast pre-condensate is converted into a water-insoluble aminoplast resin, which precipitates from the aqueous phase and deposits preferably on the surface of the cinmethylin droplets. It is possible to achieve an efficient encapsulation even with small amounts of the aminoplast pre-condensate.

Preferably, the polycondensation of the aminoplast is performed at pH of less than pH 6, in particular at a pH of at most pH 5, e.g. in the range of pH 0 to 6, more particularly in the range from pH 1 to 5 or in the range from pH 2 to 4.

The pH of the aqueous suspension is usually adjusted by addition of suitable amounts of an organic or inorganic acid, such as sulfuric acid, hydrochloric acid, phosphoric acid, a carboxylic acid including alkanoic acids, alkandioic acids or hydroxycarboxylic acids, such as formic acid, acetic acid, propionic acid, oxalic acid, malic acid or citric acid, and alkyl or arylsulfonic acids, such as methanesulfonic acid or toluenesulfonic acid. It is preferred, if at least a portion, in particular the majority of the acid is present in the aqueous suspension, before the aqueous suspension is heated to the reaction temperature.

Preferably, the polycondensation of the aminoplast pre-condensate is performed at elevated temperature, in particular at a temperature of at least 30° C., in particular at least 40° C. or at least 50° C., e.g. at a temperature in the range of 30 to 100° C., in particular in the range of 40 to 95° C. or in the range of 50 to 90° C. It may be possible to effect the start of the polycondensation of the aminoplast at a comparatively low temperature, e.g. a temperature in the range of 30 to 65° C. or 35 to 60° C. and then complete the polycondensation reaction at a higher temperature of e.g. 50 to 100° C. or 60 to 90° C. The time for completing the polycondensation may vary, depending on the reactivity of the pre-condensate, the temperature and the pH of the aqueous suspension and may take from 1 h to 24 h, in particular from 2 to 12 h. Preferably, the polycondensation reaction is at least partly performed at temperatures of at least 50° C., in particular at least 60° C., e.g. for 1 to 8 h at a temperature in the range from 50 to 100° C., in particular 60 to 90° C.

The thus obtained aqueous suspension of microparticles may be neutralized by the addition of a base.

Matrix particles are generally obtainable via a miniemulsion polymerization process using high shear forces and sufficient amounts of emulsifiers for finely dispersing the starting materials (i.e. compound to be embedded—here cinmethylin—and monomers for forming the polymer matrix) in an aqueous medium. This method is especially suitable for preparing matrix particles with a poly(meth)acrylate matrix. Preferably, the monomers (see the above definition of suitable and preferred monomers; e.g. an acrylate, methacrylate, arylic acid and/or methacrylic acid and optionally other ehylenically unsaturated monomers, such as maleic acid), cinmethylin, water, at least one emulsifier and optionally also a protective colloid are mixed, then submitted to high shear forces by using high force dispersion devices like for example a ultrasonic sound equipment or a high pressure homogenizer to obtain a miniemulsion. Addition of a free radical starter starts the polymerization reaction, which can be carried out at a temperature of from 20 to 90° C.

Similarly, matrix particles with a polystyrene matrix or an aminoplast matrix can be obtained, where in the latter case, of course no free radical starter is used, polymerization being triggered, e.g. by a pH reduction and/or by heating.

Compositions containing microcapsules or matrix particles of polymeric materials other than those explicitly described above can be prepared in an analogous manner or by processes known to those skilled in the art.

The reaction mixture of the microparticle formation may either be used as such for the further mixing step with the further herbicide, optionally after a purification step, such as filtration in order to remove possible agglomerates, or the microparticles can be first isolated and then mixed with the further herbicide, optionally after re-suspending them in a desired medium such as water or an aqueous medium. Isolation of the microparticles can be carried out by known means such as filtration or centrifugation, or the aqueous suspension may be spray-dried, granulated or freeze-dried.

The invention also relates to the use of the composition of the invention for controlling undesired vegetation, and to a method for controlling undesired vegetation comprising treating the soil in which undesired vegetation is growing and/or undesired vegetation and/or cultivated plants to be protected from undesired vegetation and/or on their environment with the composition of the invention.

The composition of the present invention is suitable for controlling a large number of undesirable vegetation (harmful plants), including monocotyledonous weeds and dicotyledonous weeds.

In one embodiment, the undesirable vegetation is selected from monocotyledonous weed species. Preferably, the undesirable vegetation is selected from the family Poaceae. More preferably, the undesirable vegetation is selected from the tribes Aveneae, Bromeae, Paniceae and Poeae. In one embodiment, the undesirable vegetation is selected from the tribe Aveneae. In another embodiment, the undesirable vegetation is selected from the tribe Bromeae. In yet another embodiment, the undesirable vegetation is selected from the tribe Paniceae. In still another embodiment, the undesirable vegetation is selected from the tribe Poeae.

In particular, the composition of the present invention may be used for controlling annual weeds such as gramineous weeds (grass weeds) including, but not limited to, the genera *Aegilops* such as *Aegilops* cylindrical (AEGCY, jointed goatgrass); *Agropyron* such as *Agropyron repens* (AGRRE, common couchgrass); *Alopecurus* such as *Alopecurus myosuroides* (ALOMY, blackgrass) or *Alopecurus aequalis* (ALOAE, foxtail); *Apera* such as *Apera spica-venti* (APESV, silky wind grass); *Avena* such as *Avena fatua* (AVEFA, wild oat) or *Avena sterilis* subsp. *Sterilis* (AVEST, sterile oat); *Brachiaria* such as *Brachiaria plantaginea* (BRAPL, Alexander grass) or *Brachiaria decumbens* (BRADC, Surinam grass); *Bromus* such as *Bromus inermis* (BROIN, awnless brome), *Bromus sterilis* (BROST, barren bromegrass), *Bromus tectorum* (BROTE, cheatgrass), *Bromus arvensis* (BROAV, field bromegrass), *Bromus secalinus* (BROSE, rye bromegrass) or *Bromus hordeacus* (BROMO, lopgrass); *Cenchrus* such as *Cenchrus echinatus* (CCHEC, Mossman River grass); *Cynodon* such as *Cynodon dactylon* (CYNDA, bermudagrass); *Digitaria* such as *Digitaria ciliaris* (DIGAD, southern crabgrass), *Digitaria sanguinalis* (DIGSA, hairy crabgrass), *Digitaria insularis* (TRCIN, sourgrass) or *Digitaria ischaemum* (DIGIS, smooth crabgrass); *Echinochloa* such as *Echinochloa colonum* (ECHCO, awnless barnyardgrass), *Echinochloa crus-galli* (ECHCG, common barnyard grass), *Echinochloa crus-pavonis* (ECHCV, Gulf cockspurgrass), *Echinochloa oryzoides* (ECHOR, early barnyardgrass) or *Echinochloa phyllogogon* (ECHPH, late barnyardgrass); *Eleusine* such as *Eleusine indica* (ELEIN, Indian goosegrass); *Eriochloa* species such as *Eriochloa villosa*, *Ischaemum* such as *Ischaemum rugusom* (ISCRU, muraina grass); *Leptochloa* such as *Leptochloa chinensis* (LEFCH, Chinese sprangletop), *Lep-*

*tochloa fascicularis* (LEFFA, salt-meadow grass), *Leptochloa filiformis* (LEFPC, thread sprangletop), *Leptochloa mucronata* (LEFFI, red sprangletop), *Leptochloa panicoides* (LEFPA, tighthead sprangletop), *Leptochloa scabra* (LEFSC) or *Leptochloa virgata* (LEFVI, tropical sprangletop); *Lolium* such as *Lolium multiflorum* (LOLMU, Italian ryegrass), *Lolium perenne* (LOLPE, English ryegrass) or *Lolium rigidum* (LOLRI, annual rye-grass); *Panicum* such as *Panicum capillare* (PANCA, tumble panicgrass), *Panicum dichotomiflorum* (PANDI, smooth witchgrass), *Panicum laevifolium* (PANLF, sweet panicgrass) or *Panicum miliaceum* (PANMI, common millet); *Phalaris* such as *Phalaris minor* (PHAMI, lesser canary grass), *Phalaris paradoxa* (PHAPA, paradoxagrass), *Phalaris canariensis* (PHACA, canarygrass) or *Phalaris brachystachys* (PHABR, short-spiked canarygrass); *Poa* such as *Poa annua* (POAAN, annual bluegrass), *Poa pratensis* (POAPR, Kentucky bluegrass) or *Poa trivialis* (POATR, rough meadowgrass); *Rottboellia* such as *Rottboellia exaltata* (ROOEX, guinea-fowl grass); *Setaria* auch as *Setaria faberi* (SETFA, giant foxtail), *Setaria glauca* (PESGL, pearl millet), *Setaria italic* (SETIT, Italian millet), *Setaria pumila* (SETPU, yellow foxtail), *Setaria verticillata* (SETVE, bristly foxtail) or *Setaria viridis* (SETVI, green foxtail); and Sorghum such as *Sorghum halepense* (SORHA, Johnson grass).

The composition of the present invention is also suitable for controlling a large number of dicotyledonous weeds, in particular broadleaf weeds including, but not limited to, *Polygonum* species such as *Polygonum convolvolus* (POLCO, wild buckwheat), *Amaranthus* species such as *Amaranthus albus* (AMAAL, tumble pigweed), *Amaranthus blitoides* (AMABL, mat amaranth), *Amaranthus hybridus* (AMACH, green pigweed), *Amaranthus palmeri* (AMAPA, Palmer amaranth), *Amaranthus powellii* (AMAPO, Powell amaranth), *Amaranthus retroflexus* (AMARE, redroot pigweed), *Amaranthus tuberculatus* (AMATU, rough-fruit amaranth), *Amaranthus rudis* (AMATA, tall amaranth) or *Amaranthus viridis* (AMAVI, slender amaranth), *Chenopodium* species such as *Chenopodium album* (CHEAL, common lambsquarters), *Chenopodium ficifolium* (CHEFI, fig-leaved goosefoot), *Chenopodium polyspermum* (CHEPO, many-seeded goosefoot) or *Chenopodium hybridum* (CHEHY, maple-leaf goosefoot), *Sida* species such as *Sida spinosa* L. (SIDSP, prickly *sida*), *Ambrosia* species such as *Ambrosia artemisiifolia* (AM BEL, common ragweed), *Acanthospermum* species, *Anthemis* species such as *Anthemis arvensis* (ANTAR, field chamomile), *Atriplex* species, *Cirsium* species, *Convolvulus* species, *Conyza* species such as *Conyza bonariensis* (ERIBO, hairy horseweed) or *Conyza canadensis* (ERICA, Canada horseweed), *Cassia* species, *Commelina* species, *Datura* species, *Euphorbia* species, Geranium species such as Geranium dissectum (GERDI, cut-leaf geranium), Geranium pusillium (GERPU, small-flower geranium) or Geranium *rotundifolium* (GERRT, round-leaved cranesbill), *Galinsoga* species, *Ipomoea* species such as *Ipomoea hederacea* (IPOHE, morningglory), *Lamium* species, Malva species, *Matricaria* species such as *Matricaria chamomilla* (MATCH, wild chamomile), *Matricaria discoidea* (MATMT, pineapple weed) or *Matricaria inodora* (MATIN, false chamomille), *Sysimbrium* species, *Solanum* species, *Xanthium* species, *Veronica* species, Viola species, *Stellaria* species such as *Stellaria media* (STEME, common chickweed), *Abutilon theophrasti* (ABUTH, velvet leaf), *Hemp sesbania* (Sesbania exaltata Cory, SEBEX, Colorado river hemp), *Anoda cristata* (ANVCR, cottonweed), *Bidens pilosa* (BIDPI, common blackjack), *Centaurea* species such as *Centaurea cyanus* (CENCY, cornflower), *Galeopsis tetrahit* (GAETE common hemp nettle), *Galium aparine* (GALAP, cleavers or goosegrass), *Galium spurium* (GALSP, false cleavers), *Galium tricornutum* (GALTC, corn cleavers), *Helianthus annuus* (HELAN, common sunflower), *Desmodium tortuosum* (DEDTO, giant beggar weed), *Kochia scoparia* (KCHSC, mock cypress), *Mercurialis annua* (MERAN, annual mercury), *Myosotis arvensis* (MYOAR, field forget-me-not), *Papaver rhoeas* (PAPRH, common poppy), *Raphanus raphanistrum, Salsola kali* (SASKA, prickly glasswort), *Sonchus arvensis* (SONAR, corn sowthistle), *Tagetes minuta* (TAGMI, Mexican marigold), *Richardia brasiliensis* (RCHBR, Brazil pusley), cruciferous weeds such as *Raphanus raphanistrum* (RAPRA, wild radish), *Sinapis alba* (SINAL, white mustard), *Sinapis arvensis* (SINAR, wild mustard), *Thlaspi arvense* (THLAR, fanweed), *Descurainia Sophia* (DESSO, flixweed), *Capsella bursa-pastoris* (CAPBP, shepherd's purse), *Sisymbrium* species such as *Sisymbrium officinale* (SSYOF, hedge mustard) or *Sisymbrium orientale* (SSYOR, oriental mustard), *Brassica kaber* (SINAR, wild mustard).

The compositions of the present invention are also suitable for controlling a large number of annual and perennial sedge weeds including *cyperus* species such as purple nutsedge (*Cyperus rotundus* L.), yellow nutsedge (*Cyperus esculentus* L.), hime-kugu (*Cyperus brevifolius* H.), sedge weed (*Cyperus microiria* Steud), rice flatsedge (*Cyperus iria* L.), and the like.

Preferably, the use and method of the invention serve for controlling at least one of the following undesired plant species: *Abutilon theophrasti, Alopercurus myosuroides, Amaranthus retroflexus, Ambrosia artemisiifolia, Apera spica-venti, Bidens pilosa, Brachiaria deflexa, Brachiaria plantaginea, Capsella bursa-pastoris, Chenopodium album, Chenopodium album, Commenline benghalensis, Digitaria sanguinales, Echinocloa crus-galli, Eleusine indica, Eriochloa villosa, Erigeron Canadensis, Lamium amplexicaule, Lamium purpureum, Matricaria inodora, Panicum dichotomiflorun, Pharbitis purpurea, Poa annua, Polygonum convolvulus, Raphanus raphanistrum Setaria lutescens, Setaria faberi, Setaria verticillata, Setaria viridis, Solanum nigrum, Sorghum halepense, Stellaria media, Veronica persica.*

More preferably, the use and method of the invention serve for controlling at least one of the following undesired plant species: *Alopecurus myosuroides, Capsella bursa-pastoris, Lamium amplexicaule, Matricaria inodora,* and/or *Raphanus raphanistrum.*

Among the above unwanted plants, *Alopecurus myosuroides* is particularly difficult to control, especially in cereal and rapeseed cultures. Surprisingly, the composition of the invention, especially the composition containing picolinafen as further herbicide, has proved to be very effective against *Alopecurus myosuroides.* Thus, in particular embodiment, the use and method of the invention serve for controlling *Alopecurus myosuroides.*

Examples of suitable crop plants which are to be protected from unwanted vegetation are cereals, for example wheat (inclusive spelt, einkorn, emmer, kamut, durum and triticale), rye, barley, oats, maize, millet, sorghum, teff, fonio, or rice; beet, for example sugar or fodder beet; pome fruit, stone fruit and soft fruit, for example apples, pears, plums, peaches, almonds, cherries, strawberries, raspberries, currants or gooseberries; legumes, for example beans, lentils, peas, lucerne or soybeans; oil crops, for example oilseed rape, mustard, olives, sunflowers, coconut, cacao, castor beans, oil palm, peanuts or soybeans; cucurbits, for example pumpkins/squash, cucumbers or melons; fiber crops, for example cotton, flax, hemp or jute; citrus fruit, for example oranges, lemons, grapefruit or tangerines; vegetable plants, for example spinach, lettuce, asparagus, cabbages, carrots, onions, tomatoes, potatoes, pumpkin/squash or capsicums; plants of the laurel family, for example avocados, cinnamon or camphor; energy crops and industrial feedstock crops, for example maize, soybeans, wheat, oilseed rape, sugar cane or oil palm; maize; tobacco; nuts; coffee; tea; bananas; wine (dessert grapes and grapes for vinification); hops; grass, for example turf; sweetleaf (*Stevia rebaudania*); rubber plants and forest plants, for example flowers, shrubs, deciduous trees and coniferous trees, and propagation material, for example seeds, and harvested produce of these plants.

Preferably, the crop plants which are to be protected from unwanted vegetation are selected from the group consisting of cereals and rapeseed, in particular from wheat, rye, barley, rice, maize, millet, sorghum, teff, fonio, oats and rapeseed.

Thus, preferably, the use and method of the invention serve for controlling undesired vegetation in cereal cultures and/or in rapeseed cultures; in particular in wheat, rye, barley, rice, maize, millet, sorghum, teff, fonio, oats and/or rapeseed cultures.

In a specific embodiment, the invention relates to the use of a composition containing microparticles which comprise cinmethylin and a polymeric material which surrounds or embeds cinmethylin; in particular microcapsules which comprise cinmethylin and a polymeric material which surrounds cinmethylin; and picolinafen for controlling at least one of the following undesired plant species: *Alopecurus myosuroides, Capsella* bursa-*pastoris, Lamium amplexicaule, Matricaria inodora*, and/or *Raphanus raphanistrum*; and in particular for controlling *Alopecurus myosuroides*. More specifically, the invention relates to the use of a composition containing microparticles which comprise cinmethylin and a polymeric material which surrounds or embeds cinmethylin; in particular microcapsules which comprise cinmethylin and a polymeric material which surrounds cinmethylin; and picolinafen for controlling at least one of the following undesired plant species: *Alopecurus myosuroides, Capsella bursa-pastoris, Lamium amplexicaule, Matricaria inodora*, and/or *Raphanus raphanistrum* in cereal and/or rapeseed cultures; and in particular for controlling *Alopecurus myosuroides* in cereal and/or rapeseed cultures.

In another specific embodiment, the invention relates to the use of a composition containing microparticles which comprise cinmethylin and a polymeric material which surrounds or embeds cinmethylin; in particular microcapsules which comprise cinmethylin and a polymeric material which surrounds cinmethylin; and quinmerac for controlling at least one of the following undesired plant species: *Alopecurus myosuroides, Capsella bursa-pastoris, Lamium amplexicaule, Matricaria inodora*, and/or *Raphanus raphanistrum*; and in particular for controlling *Alopecurus myosuroides*. More specifically, the invention relates to the use of a composition containing microparticles which comprise cinmethylin and a polymeric material which surrounds or embeds cinmethylin; in particular microcapsules which comprise cinmethylin and a polymeric material which surrounds cinmethylin; and quinmerac for controlling at least one of the following undesired plant species: *Alopecurus myosuroides, Capsella bursa-pastoris, Lamium amplexicaule, Matricaria inodora*, and/or *Raphanus raphanistrum* in cereal and/or rapeseed cultures; and in particular for controlling *Alopecurus myosuroides* in cereal and/or rapeseed cultures.

In a specific embodiment, the invention relates to the use of a composition containing microparticles which comprise cinmethylin and a polymeric material which surrounds or embeds cinmethylin; in particular microcapsules which comprise cinmethylin and a polymeric material which surrounds cinmethylin; and flufenacet for controlling at least one of the following undesired plant species: *Alopecurus myosuroides, Capsella* bursa-*pastoris, Lamium amplexicaule, Matricaria inodora*, and/or *Raphanus raphanistrum*; and in particular for controlling *Alopecurus myosuroides*. More specifically, the invention relates to the use of a composition containing microparticles which comprise cinmethylin and a polymeric material which surrounds or embeds cinmethylin; in particular microcapsules which comprise cinmethylin and a polymeric material which surrounds cinmethylin; and flufenacet for controlling at least one of the following undesired plant species: *Alopecurus myosuroides, Capsella* bursa-*pastoris, Lamium amplexicaule, Matricaria inodora*, and/or *Raphanus raphanistrum* in cereal and/or rapeseed cultures; and in particular for controlling *Alopecurus myosuroides* in cereal and/or rapeseed cultures.

In a specific embodiment, the invention relates to the use of a composition containing microparticles which comprise cinmethylin and a polymeric material which surrounds or embeds cinmethylin; in particular microcapsules which comprise cinmethylin and a polymeric material which surrounds cinmethylin; and diflufenican for controlling at least one of the following undesired plant species: *Alopecurus myosuroides, Capsella* bursa-*pastoris, Lamium amplexicaule, Matricaria inodora*, and/or *Raphanus raphanistrum*; and in particular for controlling *Alopecurus myosuroides*. More specifically, the invention relates to the use of a composition containing microparticles which comprise cinmethylin and a polymeric material which surrounds or embeds cinmethylin; in particular microcapsules which comprise cinmethylin and a polymeric material which surrounds cinmethylin; and diflufenican for controlling at least one of the following undesired plant species: *Alopecurus myosuroides, Capsella bursa-pastoris, Lamium amplexicaule, Matricaria inodora*, and/or *Raphanus raphanistrum* in cereal and/or rapeseed cultures; and in particular for controlling *Alopecurus myosuroides* in cereal and/or rapeseed cultures.

The term crop plants also includes those plants which have been modified by breeding, mutagenesis or methods, including the biotechnological agricultural products which are on the market or in the process of being developed. Genetically modified plants are plants whose genetic material has been modified in a manner which does not occur under natural conditions by hybridizing, mutations or natural recombination (i.e. recombination of the genetic material). Here, one or more genes will, as a rule, be integrated into the genetic material of the plant in order to improve the plant's properties. Such recombinant modifications also comprise posttranslational modifications of proteins, oligo- or polypeptides, for example by means of glycosylation or binding polymers such as, for example, prenylated, acetylated or farnesylated residues or PEG residues.

The composition of the invention is useful for combating undesired vegetation. For this purpose, the composition may be applied as such or is preferably applied after dilution with water. Preferably, for various purposes of end user application, a so-called aqueous spray-liquor is prepared by diluting the compositions of the present invention with water, e.g. tap water. The spray-liquors may also comprise further constituents in dissolved, emulsified or suspended form, for example fertilizers, active substances of other groups of herbicidal or growth-regulatory active substances, further active substances, for example active substances for controlling animal pests or phytopathogenic fungi or bacteria, furthermore mineral salts which are employed for alleviating nutritional and trace element deficiencies, and non-phytotoxic oils or oil concentrates. These agents can be admixed with the compositions according to the invention in a weight ratio of 1:100 to 100:1, preferably 1:10 to 10:1. As a rule, these constituents are added to the spray mixture before, during or after dilution of the compositions according to the invention. The composition according to the invention is usually applied from a predosage device, a knapsack sprayer, a spray tank, a spray plane, or an irrigation system. Usually, 20 to 2000 liters, preferably 50 to 400 liters, of the ready-to-use spray liquor are applied per hectare of agricultural useful area.

The composition of the invention can be applied by the pre-emergence or the post-emergence method. If one of the active compounds is less well tolerated by certain crop plants, application techniques may be employed where the herbicidal compositions are sprayed, with the aid of the spraying apparatus, in such a way that the leaves of the sensitive crop plants ideally do not come into contact with them, while the active substances reach the leaves of undesired plants which grow underneath, or the bare soil surface (post-directed, lay-by).

Various types of oils, wetters, adjuvants, fertilizer, or micronutrients, and further pesticides (e.g. herbicides, insecticides, fungicides, growth regulators, safeners) may be added to the compositions comprising them as premix or, if appropriate not until immediately prior to use (tank mix). These agents can be admixed with the compositions according to the invention in a weight ratio of 1:100 to 100:1, preferably 1:10 to 10:1.

The composition of the invention is generally applied in such amounts that the amounts of cinmethylin applied are, depending on the kind of effect desired, from 0.001 to 2 kg per ha, preferably from 0.005 to 2 kg per ha, more preferably from 0.05 to 0.9 kg per ha, in particular from 0.05 to 0.6 kg per ha.

The present invention has various advantages. The composition is stable during storage for a long time, even at a wide temperature range. Especially sediment formation, agglomeration, crystallization and syneresis as observed with compositions containing "naked" cinmethylin which is not comprised in microparticles and further herbicides do not occur. Moreover, phytotoxicity is not increased. At the same time, the herbicidal activity of the composition is high.

The invention is now further illustrated by the following examples.

EXAMPLES

In the examples, cinmethylin refers to the racemic mixture (±)-2-exo-(2-methylbenzyloxy)-1-methyl-4-isopropyl-7-oxabicyclo[2.2.1]heptane.

A. Synthetic Examples

1. Preparation of a Composition Containing Quinmerac
1.1 Preparation of Microcapsules An aqueous phase was prepared by mixing 50 g of 1,2-propylene glycol (as antifreeze), 12 g of Reax® 88B (sodium salt of a chemically modified low molecular weight kraft lignin polymer solubilized by five sulfonate groups; a dispersant from MeadWestvaco Corporation) and 6 g of Wettol® NT1 (a wetting agent from BASF) with 400 g of water under stirring at room temperature.

An oily phase was prepared by mixing 450 g of cinmethylin and 20.45 g of Basonat® HW 100 (trimer of hexamethylene diisocyanate; from BASF).

The oily phase was poured into the aqueous phase. The mixture was homogenized by first mixing with an Ultraturrax for 60 s, then at 14000 rpm for 15 s, then mixing with a Viskojet at 200 rpm. 5.36 g of hexamethylene diamine was added at a rate of 15 ml/min. The mixture was stirred at 250 rpm for 2 h at room temperature, then 1.5 g of Rhodopol® G (a xanthan gum thickener from Rhodia), and 2 g of Acticide® MBS (a bactericide from Thor GmbH), dispersed in 10% of water, were added and stirring was continued for a further hour at 280 rpm. Acetic acid was added under stirring at 350 rpm until pH 7-8 was reached. Then 2 g of Wacker-Silicon SRE-PFL (an antifoam from Wacker) was rapidly added. Finally water was added to give 1 L of suspension. The obtained mixture was filtered over a 150 μm sieve.

1.2 Preparation of Quinmerac Premix

A mixture of 36 g of Pluronic® PE 10500 (a dispersant; EO/PO block copolymer; from BASF) and 53.3 g of 1,2-propylene glycol were dissolved in 400 g of water. Then successively 12 g of Wettol® D1 (a dispersant), 600 g of quinmerac and 1.36 g of Wacker-Silicon SRE-PFL were added and the resulting mixture was milled on a Bachofen Dyno® mill with 0.75-1.00 mm glass beads until 80% of the particles were below 2 μm. 2.14 g of Acticide® MBS and 1.61 g of Rhodopol® G were added and the mixture was stirred overnight. Then 3.18 g of Wacker-Silicon SRE-PFL was rapidly added. Finally water was added to give 1 L of suspension. The obtained mixture was filtered over a 150 μm sieve.

1.3 Preparation of a Composition Containing Cinmethylin Microcapsules and Quinmerac 581 g of the composition obtained in example 1.1 and 510 g of the composition obtained in example 1.2 were mixed. The resulting composition contained 250 g/l of cinmethylin and 250 g/l of quinmerac.

2. Preparation of a Composition Containing Picolinafen
2.1 Preparation of Picolinafen Premix A mixture of 83.4 g of Morwet® D425 (a dispersant; a sodium salt of naphthalene sulfonate condensate; from AkzoNobel), 51.24 g of Ethylan® NS 500 K (non-ionic surfactant; polyalkoxylated butyl ether; from AkzoNobel) and 220.8 g of 1,2-propylene glycol were dissolved in 450 ml of water. Then successively 540 g of picolinafen and 2.43 g of Wacker-Silicon SRE-PFL were added and the resulting mixture was milled on a Bachofen Dyno® mill with 0.75-1.00 mm glass beads until 80% of the particles were below 2 μm. 5.67 g of Wacker-Silicon SRE-PFL was rapidly added. Finally water was added to give 1 L of emulsion. The obtained mixture was filtered over a 150 μm sieve.

2.2 Preparation of a Composition Containing Cinmethylin Microcapsules and Picolinafen The composition obtained in example 1.1 and the composition obtained in example 2.1 were mixed, then further bactericide (final concentration: 2.06 g/l) and thickener (final concentration: 1.55 g/l) was added. The resulting composition contained 400 g/l of cinmethylin and 40 g/l of picolinafen.

B. Use Examples

B.1 Crystal Growth

A part of the composition of example 1.3 was kept at 40° C. for 2 weeks, and another part at 54° C., also for 2 weeks. The average particle size of the suspended particles was determined directly after preparing the composition of example 1.3 and after storage. The average particle size was determined via static light diffraction with a Malvern Mastersizer 2000. The particle size and particle size distribution was unchanged after 2 weeks of storage at both 40° C. and 54° C.; i.a. no particle growth of the quinmerac particles was observed.

As comparison, a suspoemulsion was prepared from an emulsion concentrate (EC) of cinmethylin (i.e. cinmethylin not present in microcapsules) and a suspension concentrate (SC) of quinmerac. The suspoemulsion contained the active compounds in the same concentration as the composition of example 1.3 (i.e. 250 g/l of cinmethylin and 250 g/l of quinmerac) and further the following components: Wacker-Silicon SRE-PFL (4 g/l), 1,2-propylene glycol (65 g/l), Acticide® MBS (2 g/l), Pluronic® PE 10500 (15 g/l), Rhodopol® G (1.5 g/l), Soprophor BSU (15 g/l; adjuvant), Wettol® D1 (5 g/l), Wettol® EM 1 (25 g/l, emulsifier), Wettol® EM 31 (10 g/l, emulsifier), Solvesso® 200 ND (39.5 g/l; diluent) and water ad 1 l). A part of this suspoemulsion was kept at 40° C. for 2 weeks, and another part at 54° C., also for 2 weeks. Strong crystal growth of quinmerac particles was observed, reflected in an increase of the $d_{90}$ value from originally 5 μm to 12 μm after the two weeks storage.

B.2 Herbicidal Activity and Phytotoxicty

The effect of the herbicidal composition of cinmethylin and picolinafen as a mixed formulation of a capsule suspension (cinmethylin CS) and a suspension concentrate (picolinafen SC), prepared according to synthesis example 2.2 (termed below ZC), on the growth of both undesirable and cultivated plants was tested in the following field experiments and compared to the active compounds as applied alone (solo application) or applied as a mixture in form of an emulsifiable concentrate containing cinmethylin in non-encapsulated form and picolinafen:

Winter wheat was seeded in different soils ranging from sandy loam to clay loam soil containing 2.1-5.5% of organic matter.

For the post emergence treatment, the plants were first grown up to the 2 leaf stage (BBCH 12). Here, the herbicidal compositions were suspended or emulsified in water as distribution medium and sprayed using finely distributing nozzels.

Cinmethylin was used in the solo application as an emulsion concentrate with an active ingredient concentration of 750 g/l.

Picolinafen was used in the solo application as a commercial extruded granule (WG) formulation having an active ingredient concentration of 75% (Sniper S®).

The mixture of cinmethylin and picolinafen as an emulsifiable concentrate was prepared from cinmethylin as an emulsifiable concentrate (EC) and picolinafen as a water dispersable granule (WG) having an active ingredient concentration of 500 g/l and 50 g/l, respectively.

The mixture of cinmethylin and picolinafen as a mixed formulation of a capsule suspension (cinmethylin CS) and a suspension concentrate (picolinafen SC) was prepared according to synthesis example 2.2 having a concentration of 400 g/l and 40 g/l, respectively.

The herbicidal activity for the individual herbicidal compositions (solo and mixture applications) was assessed 31 days after treatment (DAT).

The evaluation for the damage on winter wheat and undesired weeds caused by the tested compositions was carried out using a scale from 0 to 100%, compared to the untreated control plants. Here, 0 means no damage and 100 means complete destruction of the plants.

The plants used in the greenhouse experiments belonged to the following species:

| EPPO Code | Scientific name |
|---|---|
| ALOMY | Alopecurus myosuroides |
| CAPBP | Capsella bursa-pastoris |
| LAMAM | Lamium amplexicaule |
| MATIN | Matricaria inodora |
| RAPRA | Raphanus raphanistrum |
| TRZAW | Triticum aestivum |

Table 1 below relates to the herbicidal activity and phytotoxicity in field trials of the individual actives and the combinations applied at different rates and ratios, in post-emergence application at 31 days after treatment (DAT).

TABLE 1

Part 1: Solo applications

| | cinmethylin (EC) (solo) | | picolinafen (WG) (solo) | |
|---|---|---|---|---|
| Plant | use rate [g ai/ha] | herbicidal activity [%] | use rate [g ai/ha] | herbicidal activity [%] |
| ALOMY | 500 | 100 | 50 | 0 |
| CAPBP | 500 | 65 | 50 | 96 |
| LAMAM | 500 | 53 | 50 | 94 |
| MATIN | 500 | 62 | 50 | 69 |
| RAPRA | 500 | 10 | 50 | 98 |
| TRZAW | 500 | 0 | 50 | 0 |
| TRZAW | 1000 | 0 | 100 | 0 |

Part 2: Combined applications

| | combination (EC) cinmethylin + picolinafen | | combination (ZC*) cinmethylin + picolinafen | |
|---|---|---|---|---|
| Plant | use rate [g ai/ha] | herbicidal activity [%] | use rate [g ai/ha] | herbicidal activity [%] |
| ALOMY | 500 + 50 | 100 | 500 + 50 | 100 |
| CAPBP | 500 + 50 | 98 | 500 + 50 | 95 |
| LAMAM | 500 + 50 | 97 | 500 + 50 | 93 |
| MATIN | 500 + 50 | 94 | 500 + 50 | 72 |
| RAPRA | 500 + 50 | 98 | 500 + 50 | 98 |
| TRZAW | 500 + 50 | 4 | 500 + 50 | 1 |
| TRZAW | 1000 + 100 | 12 | 1000 + 100 | 1 |

* ZC: mixed formulation of a capsule suspension (CS) of cinmethylin and a suspension concentrate (SC) of picolinafen according to example 2.2

As can be seen, the mixture of cinmethylin and picolinafen as an emulsifiable concentrate, containing cinmethylin in non-encapsulated form, shows significant phytotoxicity. In contrast, the mixed formulation of a capsule suspension of cinmethylin (CS) and a suspension concentrate of picolinafen (SC), prepared according to synthesis example 2.2, shows nearly no phytotoxicity, whilst maintaining efficacy on grasses and broad leaf weeds.

We claim:

1. A composition comprising
   (a) microparticles which comprise cinmethylin and a polymeric material which surrounds or embeds cinmethylin; and
   (b) an herbicide different from cinmethylin and selected from the group of picolinafen, diflufenican, and flufenacent, wherein the herbicide different from cinmethylin is not enclosed in the microparticle.

2. The composition of claim 1, wherein cinmethylin and the herbicide different therefrom are present in a weight ratio of from 100:1 to 1:100.

3. The composition of claim 1, wherein the microparticles are selected from the group consisting of
    microcapsules comprising a shell and a core, where the core comprises cinmethylin and the shell comprises a polymeric material;
    matrix particles containing a polymeric material in form of a polymer matrix in which cinmethylin is embedded; and
    mixed forms thereof.

4. The composition of claim 1, wherein the polymeric material is selected from the group consisting of polyureas, polyurethanes, poly(meth)acrylates, aminoplasts, polystyrenes, polyamides, polysulfonamides, polyesters and polycarbonates.

5. The composition of claim 4, wherein the polymeric material is selected from the group consisting of polyureas, poly(meth)acrylates and aminoplasts.

6. The composition of claim 3, wherein the microparticles are microcapsules comprising a shell and a core, wherein the core comprises cinmethylin and the shell comprises polyurea obtainable by polyaddition reaction of at least one aliphatic or aromatic polyisocyanate and at least one aliphatic or aromatic polyamine.

7. The composition of claim 3, wherein in the microcapsules the weight ratio of cinmethylin and the polymeric material comprised in the shell is of from 1:1 to 80:1, and in the matrix particles the weight ratio of cinmethylin and the polymeric material forming the polymer matrix is of from 10:1 to 1:10.

8. The composition of claim 1, wherein the average particle size d50 of the microparticles, as determined according to ISO 13320:2009, Particle Size Analysis—Laser Diffraction Methods, is from 0.05 to 100 µm.

9. The composition of claim 8, wherein the average particle size d50, as determined according to ISO 13320:2009, Particle Size Analysis—Laser Diffraction Methods, is from 0.5 to 100 µm when the microparticles are microcapsules, and the average particle size d50 is of from 50 nm to 1 µm when the microparticles are matrix particles.

10. The composition of claim 1, containing the microparticles in an amount of from 10 to 70% by weight, based on the total weight of the composition.

11. The composition of claim 1, which is an aqueous dispersion.

12. The composition of claim 1 further comprising a surfactant, further dispersing agent, emulsifier, wetting agent, further adjuvant, solubilizer, penetration enhancer, protective colloid, adhesion agent, thickener, humectant, antifoam, antifreeze agent, stabilizer, antimicrobial agent, pigment, colorant, buffer, tackifier or binder.

13. A method for preparing the composition of claim 1 comprising polymerizing one or more monomers or curing a pre-polymer or pre-condensate in the presence of the cinmethylin, and mixing with the herbicide different from cinmethylin.

14. The composition of claim 3, wherein the microparticles are microcapsules.

* * * * *